United States Patent
Chen et al.

(10) Patent No.: US 10,342,976 B2
(45) Date of Patent: Jul. 9, 2019

(54) SYSTEMS AND METHODS FOR FACILITATING INTERAURAL TIME DIFFERENCE PERCEPTION BY A BINAURAL COCHLEAR IMPLANT PATIENT

(71) Applicants: ADVANCED BIONICS AG, Staefa (CH); Chen Chen, Valencia, CA (US); Leonid M. Litvak, Los Angeles, CA (US)

(72) Inventors: Chen Chen, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/741,217

(22) PCT Filed: Jun. 30, 2016

(86) PCT No.: PCT/US2016/040332
§ 371 (c)(1),
(2) Date: Dec. 29, 2017

(87) PCT Pub. No.: WO2017/011196
PCT Pub. Date: Jan. 19, 2017

(65) Prior Publication Data
US 2018/0193642 A1   Jul. 12, 2018

Related U.S. Application Data

(60) Provisional application No. 62/191,293, filed on Jul. 10, 2015.

(51) Int. Cl.
*H04R 25/00* (2006.01)
*A61N 1/36* (2006.01)

(52) U.S. Cl.
CPC ..... *A61N 1/36038* (2017.08); *A61N 1/36036* (2017.08); *H04R 25/407* (2013.01);
(Continued)

(58) Field of Classification Search
CPC ...... H04R 25/00; H04R 25/55; H04R 25/558; H04R 2225/49; H04R 2460/01
(Continued)

(56) References Cited

U.S. PATENT DOCUMENTS 7,920,923 B2   4/2011   Laback et al.
9,283,376 B2   3/2016   Wouters et al.
(Continued)

FOREIGN PATENT DOCUMENTS

WO   2002/096153   11/2002
WO   2010/115227   10/2010
WO   2013/164511   11/2013

OTHER PUBLICATIONS

International Search Report and Written Opinion received in International Application No. PCT/US16/040332, dated Sep. 14, 2016.

*Primary Examiner* — Suhan Ni
(74) *Attorney, Agent, or Firm* — ALG Intellectual Property, LLC

(57) ABSTRACT

A binaural cochlear implant system (system) includes first and second microphones associated with first and second ears of a patient, respectively. The microphones detect an audio signal presented to the patient and output first and second signals representative of the audio signal as detected at the first and second ears, respectively. The system also includes a first sound processor that receives the first signal from the first microphone and the second signal from a second sound processor by way of a communiation link with the second sound processors. The first sound processor generates first and second fine structure signals representa- (Continued)

tive of fine structure information of the first and second fine structure signals, respectively, and generates a timing pulse signal based on the first and second fine structure signals. The first sound processor uses the timing pulse signal to represent to the patient an interaural time difference between the first and second signals.

20 Claims, 12 Drawing Sheets

(52) U.S. Cl.
CPC ......... *H04R 25/552* (2013.01); *H04R 25/554* (2013.01); *H04R 2225/43* (2013.01); *H04R 2225/67* (2013.01)

(58) Field of Classification Search
USPC .......................... 381/312–313, 315–317, 320
See application file for complete search history.

(56) References Cited

U.S. PATENT DOCUMENTS

| | | | |
|---|---|---|---|
| 9,693,155 B2* | 6/2017 | Meister | H04R 25/552 |
| 9,776,001 B2* | 10/2017 | Meister | A61N 1/36036 |
| 2008/0319509 A1 | 12/2008 | Laback | |
| 2009/0264961 A1 | 10/2009 | Schleich et al. | |
| 2012/0303093 A1 | 11/2012 | Wouters et al. | |
| 2014/0052217 A1 | 2/2014 | Smith | |
| 2014/0219486 A1 | 8/2014 | Brown | |
| 2014/0222104 A1 | 8/2014 | Smith | |

\* cited by examiner

SYSTEMS AND METHODS FOR FACILITATING INTERAURAL TIME DIFFERENCE PERCEPTION BY A BINAURAL COCHLEAR IMPLANT PATIENT

RELATED APPLICATIONS

The present application claims priority to U.S. Provisional Patent Application No. 62/191,293, filed Jul. 10, 2015. The contents of the provisional patent application are hereby incorporated by reference in their entirety.

BACKGROUND INFORMATION

One way that spatial locations of sound sources may be resolved is by a listener perceiving an interaural time difference ("ITD") in the arrival of a sound to each of the two ears of the listener. For example, if the listener perceives that a sound arrives at his or her left ear prior to arriving at his or her right ear, the listener may determine, based on the ITD of the sound's arrival to each ear, that the spatial location of the sound source is to the left of the listener. The relative magnitude of the ITD may further indicate to the listener whether the sound source is located slightly to the left of center (in the case of a relatively small ITD) or further to the left (in the case of a larger ITD). In this way, listeners may use ITD cues along with other types of cues to spatially locate various sound sources in the world around them, as well as to segregate and/or distinguish the sound sources from noise and/or from other sound sources.

Unfortunately, many cochlear implant systems are not configured to encode ITD cues in representations of sound provided to cochlear implant patients relying on the cochlear implant systems, and, as a result, it may be difficult for the cochlear implant patients to spatially locate sound sources around themselves or to segregate and/or distinguish particular sound sources from other sound sources or from noise in the environment surrounding the patients. Even cochlear implant systems that have attempted to encode ITD cues into representations of sound provided to cochlear implant patients have been of limited use in enabling the cochlear implant patients to successfully and easily locate the sound sources around them. For example, cochlear implant systems may encode ITD cues onto signals that are presented to patients with timing that is unrelated to the sound being represented or that is related to the sound in a non-ideal way that makes the ITD less natural and/or more difficult for the patient to perceive. Additionally, cochlear implant systems attempting to preserve ITD cues may encode the ITD cues onto signals at stimulation pulse rates that, while appropriate for reproducing sound content, may be too high for patients to successfully or easily perceive the ITD cues.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
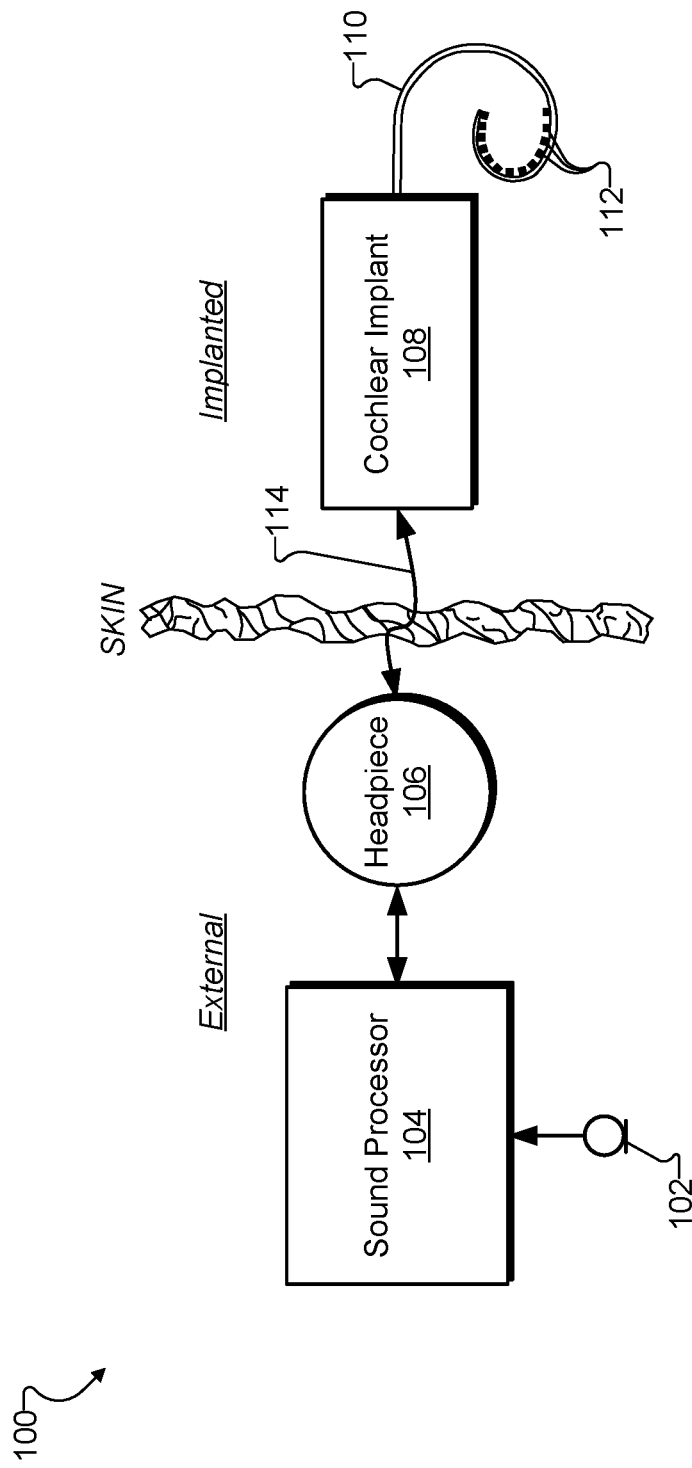
FIG. 1 illustrates an exemplary cochlear implant system according to principles described herein.

Systems and methods for facilitating interaural time difference ("ITD") perception by a binaural cochlear implant patient are described herein. For example, as will be illustrated and described in more detail below, a binaural cochlear implant system used by a cochlear implant patient may include a first microphone associated with (e.g., located within a vicinity of) a first ear of the patient and a second microphone associated with (e.g., located within a vicinity of) a second ear of the patient. While an audio signal (i.e., a combination of sounds from one or more sound sources within hearing distance of the patient) is being presented to the patient, the first microphone may detect the audio signal at the first ear and output a first signal representative of the audio signal as detected by the first microphone at the first ear. Additionally, while the audio signal is being presented to the patient, the second microphone may similarly detect the audio signal at the second ear and output a second signal representative of the audio signal as detected by the second microphone at the second ear.

The binaural cochlear implant system may further include a first sound processor associated with the first ear of the patient and a second sound processor associated with the second ear of the patient. As such, the first sound processor may be communicatively coupled directly to the first microphone, while the second sound processor may be communicatively coupled directly to the second microphone. The first sound processor and the second sound processor may also be communicatively coupled with one another by way of a communication link (e.g., a wireless audio transmission link) over which the first signal representative of the audio signal as detected by the first microphone at the first ear and the second signal representative of the audio signal as detected by the second microphone at the second ear may be exchanged between the sound processors. By each processing both the first signal and the second signal, the sound processors may present representations of the audio signal to the patient in a way that preserves ITD cues and facilitates ITD perception by the patient.

For example, the first sound processor may receive the first signal directly from the first microphone and receive the second signal from the second sound processor by way of the communication link. The first sound processor may generate a first fine structure signal representative of fine structure information of the first signal, and generate a second fine structure signal representative of fine structure information of the second signal. As used herein, "fine structure information" includes information contained in a signal (e.g., the audio signal detected by the first and second microphones at the first and second ears of the patient, the first and/or second signals representative of the audio signal, etc.) other than an envelope of the signal. For example, as will be described in more detail below, the fine structure information may include one or more peaks representative of sound waves of varying amplitudes detected by the microphones at specific times. As such, fine structure information may be represented by relatively fast amplitude fluctuations in a waveform of the signal as compared to amplitude fluctuations of the envelope of the signal.

Based on the first fine structure signal and the second fine structure signal generated from the first and second signals representative of the audio signal as detected at the first and second ears, respectively, the first sound processor may generate a first timing pulse signal. The first sound processor may then use the first timing pulse signal to represent, to the patient, an ITD between the first signal output by the first microphone and the second signal output by the second microphone. The first timing pulse signal may be generated based on the first fine structure signal and the second fine structure signal and may be used to represent the ITD in any way as may serve a particular implementation. Examples of timing pulse signals and how the timing pulse signals are used to represent the ITD to the patient will be provided below.

In a similar way, the second sound processor may also receive the first and second signals representative of the audio signal, although, in this case, the first signal may be received by way of the communication link, while the second signal may be received directly from the second microphone. Like the first sound processor, the second sound processor may generate first and second fine structure signals representative of the fine structure information of the first and second signals, respectively, and, based on the first and second fine structure signals, may generate and use a second timing pulse signal to represent the ITD to the patient. For example, the timing pulse signals may include corresponding timing pulses that are slightly offset to represent the ITD between the arrival time of the audio signal to the first ear and the arrival time of the audio signal to the second ear.

Accordingly, cochlear implants implanted within the patient may each apply electrical stimulation representative of the audio signal to a first cochlea and a second cochlea of the patient based on an electrode firing pattern determined, respectively, by the timing pulses included in the first timing pulse signal and by the corresponding timing pulses included in the second timing pulse signal. As used herein, an "electrode firing pattern" refers to a pattern of when stimulation pulses representative of an audio signal (e.g., the audio signal detected by the first and second microphones) are delivered by a binaural cochlear implant system to electrodes implanted within respective cochleas of the patient in order to present the audio signal to the patient. An electrode firing pattern may affect a patient's perception of various characteristics of an audio signal presented to the patient. For example, by incorporating fine structure information contained within an audio signal into different electrode firing patterns for each cochlear implant (e.g., by using the fine structure information to determine two different electrode firing patterns to be used by a cochlear implant system), a cochlear implant system may facilitate the patient's perception of ITD and/or otherwise improve the listening experience of the patient.

By facilitating ITD perception by binaural cochlear implant patients as described herein, binaural cochlear implant systems may provide several benefits to the binaural cochlear implant patients using the binaural cochlear implant systems. For example, by encoding ITD cues into stimulation applied to the patients, binaural cochlear implant systems may help the patients better sense the world around them by, for example, more accurately, easily, and/or conveniently determining spatial locations of various sources of sound surrounding them in the world. Additionally, encoding ITD cues into stimulation may allow patients to more easily and successfully separate, segregate, and/or perceive sounds concurrently generated by multiple sound sources (e.g., in an environment with lots of background noise, in a situation where multiple people are speaking at once, etc.).

Moreover, by encoding the ITD cues into the stimulation based on fine structure information of audio signals as described herein, binaural cochlear implant systems may make it easier for a patient to perceive the ITD than, for example, if the patient were using a system that encoded ITD cues into the stimulation without relating it to the signal (e.g., based on a constant-rate electrode firing pattern) and/or based on signal elements other than fine structure (e.g., based on an envelope of the audio signal). For example, by distinguishing sounds that generate related fine structure peaks that are detectable at each ear of the patient from sounds that generate fine structure peaks only detected at one ear of the patient, the binaural cochlear implant systems described herein may facilitate the patient in perceiving a "dominant" sound source and/or in filtering out noise and/or other sounds unrelated to the dominant sound source. Similarly, delivery of fine structure information to a cochlear implant patient (e.g., by incorporating the fine structure information into the electrode firing pattern utilized by the binaural cochlear implant system to encode ITD cues) may facilitate the patient not only in perceiving ITD, but also in perceiving temporal pitch (e.g., musical and/or vocal pitch), in compensating for low temporal resolution, and/or in other ways that may improve the listening experience of the patient.

Additionally, by generating and using (e.g., basing electrode firing patterns on) timing pulse signals that are based on not only an audio signal as detected at one ear of a patient, but by the audio signal as detected at both ears of the patient, a binaural cochlear implant system may effectively represent ITD of the audio signal using ITD stimulation at a relatively low stimulation pulse rate. While stimulation pulse rates (i.e., rates at which stimulation current is applied to the patient) of traditional electrode firing patterns may be relatively high (e.g., greater than 1000 pulses per second), many patients may struggle to perceive ITD between signals when ITD stimulation is applied at a pulse rate that is greater than a relatively low threshold (e.g., greater than approximately 200 pulses per second). As a result, it may be undesirable to present ITD stimulation current to a patient at a stimulation pulse rate like those of traditional electrode firing patterns because the pulse rate would be too fast for the patient to effectively perceive the ITD cues. Rather, to optimize and/or improve the patient's ability to perceive the ITD cues, a relatively low pulse rate (e.g., less than approximately 200 pulses per second) may be desirable for ITD stimulation. As will be described below, by each analyzing and comparing how an audio signal is detected at both ears, the sound processors in a binaural cochlear implant system may direct stimulation to be applied at a pulse rate that is regulable (i.e., that can be set to a suitably low pulse rate) while also providing stimulation only at the most advantageous times (e.g., determined by the fine structure information).

Various embodiments will now be described in more detail with reference to the figures. The disclosed methods and systems may provide one or more of the benefits mentioned above and/or various additional and/or alternative benefits that will be made apparent herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 (also referred to as an implantable cochlear stimulator) and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone such as a T-MIC™ microphone from Advanced Bionics. Microphone 102 may be associated with a particular ear of the patient such as by being located in a vicinity of the particular ear (e.g., within the concha of the ear near the entrance to the ear canal). In some examples, microphone 102 may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleas of a patient, it will be understood that stimulation current may also be applied to other suitable nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links. In the same or other examples, sound processor 104 may transmit (e.g., wirelessly transmit) information such as an audio signal detected by microphone 102 to another sound processor (e.g., a sound processor associated with another ear of the patient). For example, as will be described in more detail below, the information may be transmitted to the other sound processor by way of a wireless audio transmission link (not explicitly shown in FIG. 1).

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
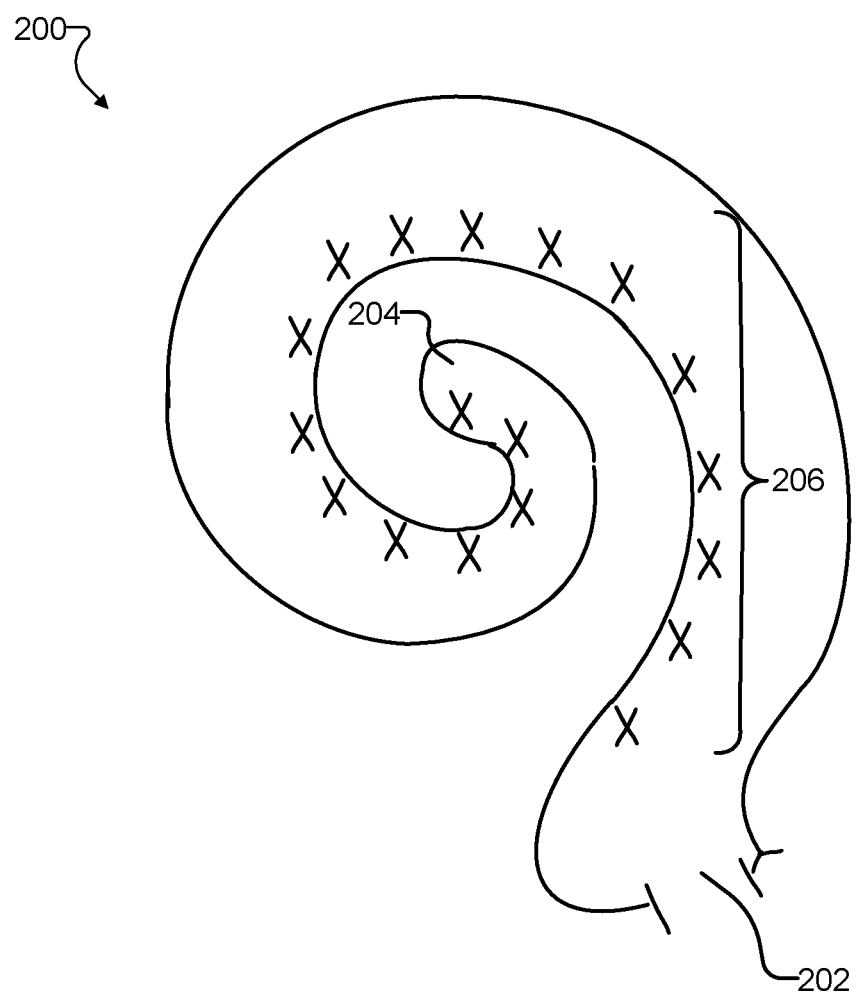
FIG. 2 illustrates a schematic structure of the human cochlea according to principles described herein.

FIG. 2 illustrates a schematic structure of the human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. Auditory nerve tissue 206 is organized within cochlea 200 in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 100 may therefore be configured to apply electrical stimulation to different locations within cochlea 200 (e.g., different locations along auditory nerve tissue 206) to provide a sensation of hearing to the patient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the patient to perceive a different frequency than the same stimulation current applied to a different electrode 112 (e.g., an electrode 112 located at a different part of auditory nerve tissue 206 within cochlea 200).

Figure 3:
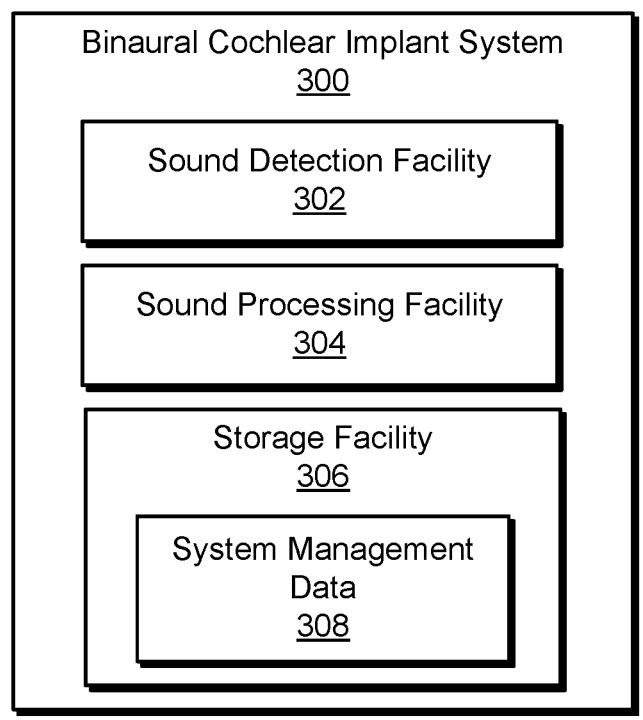
FIG. 3 illustrates exemplary components of an exemplary binaural cochlear implant system for facilitating interaural time difference ("ITD") perception by a binaural cochlear implant patient according to principles described herein.

FIG. 3 illustrates exemplary components of an exemplary binaural cochlear implant system 300 ("system 300") for facilitating ITD perception (e.g., perception of ITD cues within audio signals) by a binaural cochlear implant patient. As shown, system 300 may include, without limitation, a sound detection facility 302, a sound processing facility 304, and a storage facility 306 selectively and communicatively coupled to one another. It will be recognized that although facilities 302 through 306 are shown to be separate facilities in FIG. 3, facilities 302 through 306 may be combined into fewer facilities, such as into a single facility, or divided into more facilities as may serve a particular implementation. Each of facilities 302 through 306 will now be described in more detail.

Sound detection facility 302 may include any hardware and/or software used for capturing audio signals presented to a patient associated with system 300 (e.g., using system 300). For example, sound detection facility 302 may include two microphones (e.g., microphones similar to microphone 102 described above in relation to FIG. 1) and hardware equipment and/or software associated with the microphones. Each microphone may be associated with one of the ears of the patient such as by being positioned in a vicinity of the ear of the patient as described above. Sound detection facility 302 may detect an audio signal presented to the patient (e.g., a signal including sounds from the world around the patient) at both ears of the patient, and may provide two separate signals (i.e., separate signals representative of the audio signal as detected at each of the ears) to sound processing facility 304. Examples of microphones used to implement sound detection facility 302 and signals output by the microphones will be described in more detail below.

Sound processing facility 304 may include any hardware and/or software used for receiving the signals output from sound detection facility 302 (i.e., the signals representative of the audio signal presented to the patient as detected at both ears of the patient), and generating two separate fine structure signals representative of fine structure information of the two signals received from sound detection facility 302, respectively. Sound processing facility 304 may further include hardware and/or software for generating and using respective timing pulse signals to represent an ITD between the signals received from sound detection facility 302 (i.e., an ITD of respective arrival times of the audio signal at each ear of the patient). For example, as will be described in more detail below, the respective timing pulse signals may each include corresponding timing pulses slightly offset from one another so as to cause stimulation current to be applied at slightly different times to the patient to simulate the ITD of the audio signal arriving at the patient's ears. Sound processing facility 304 may be implemented in any way as may serve a particular implementation. In some examples, sound processing facility 304 may include or be implemented by two sound processors (e.g., sound processors similar to sound processor 104 described above in relation to FIG. 1) associated with each ear of the patient and communicatively coupled to one another via a communication link, or by a single sound processor configured to process signals detected at microphones associated with both ears of the patient.

Storage facility 306 may maintain system management data 308 and/or any other data received, generated, managed, maintained, used, and/or transmitted by facilities 302 or 304 in a particular implementation. System management data 308 may include audio signal data, fine structure signal data, pulse timing signal data, and so forth, as may be used by facilities 302 or 304 in a particular implementation.

Figure 4:
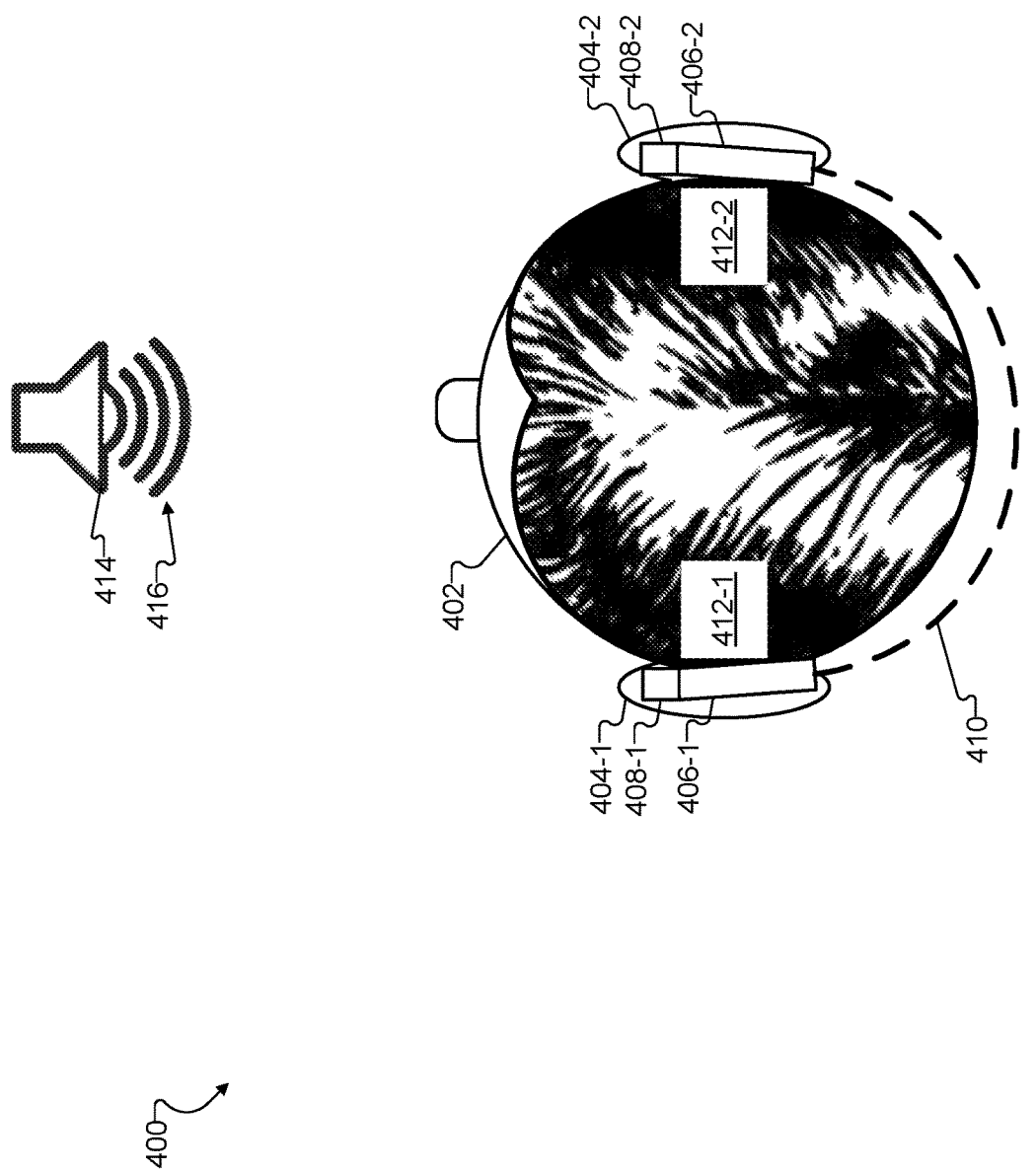
FIGS. 4-6 illustrate an exemplary implementation of the binaural cochlear implant system of FIG. 3 positioned in different orientations with respect to exemplary spatial locations of different exemplary sound sources according to principles described herein.
Figure 5:
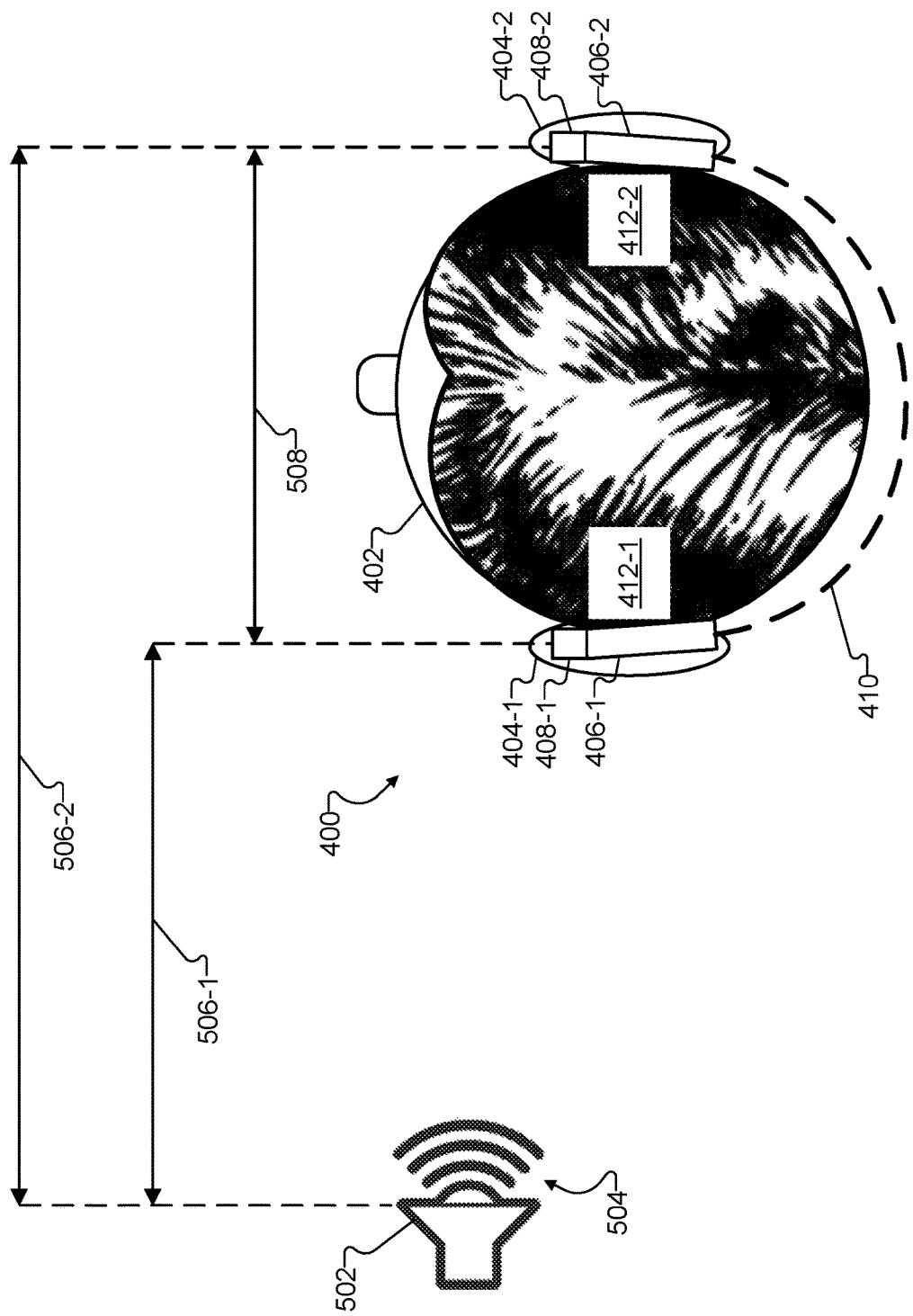
Figure 6:
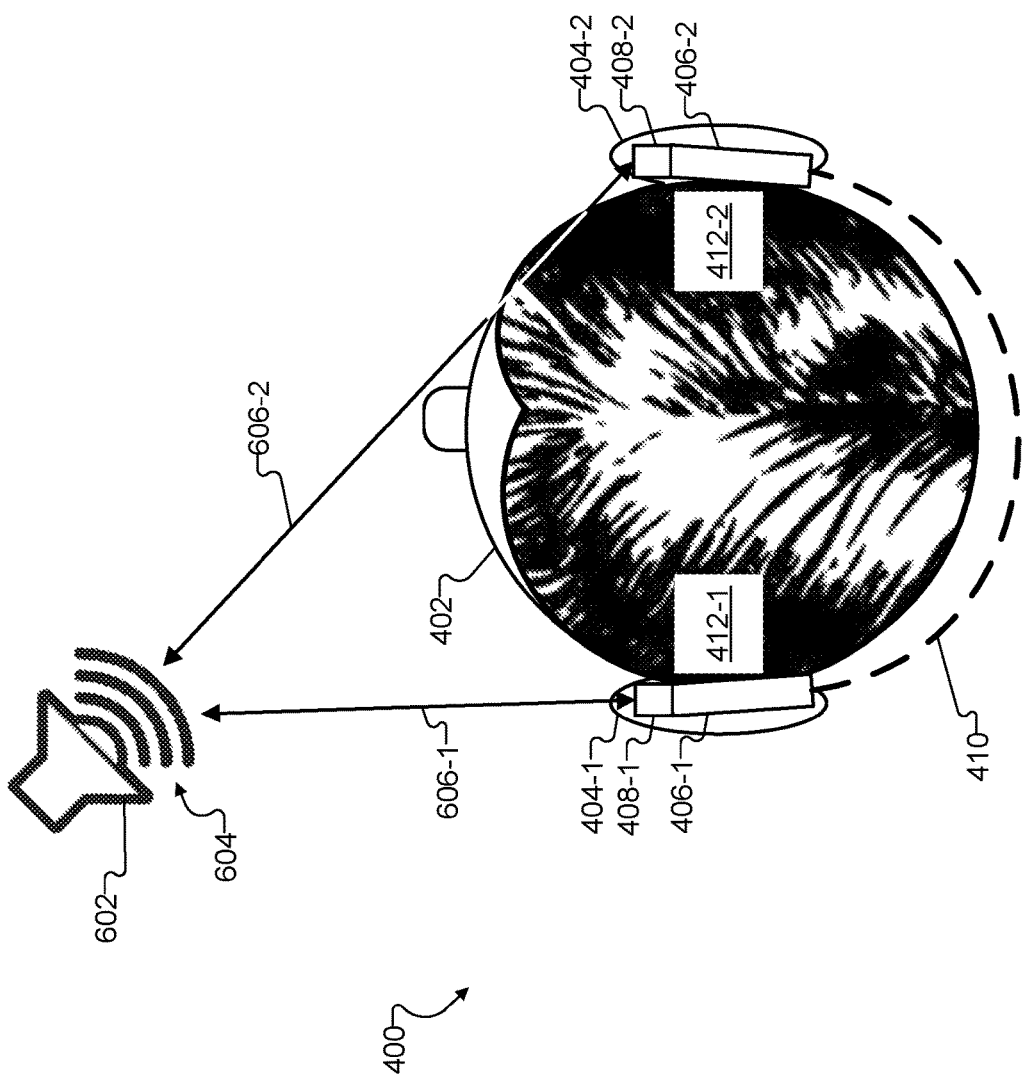

To illustrate how system 300 (e.g., one or more components of system 300) may be used to facilitate ITD perception by a binaural cochlear implant patient, FIGS. 4-6 illustrate an exemplary implementation 400 of system 300 positioned in different orientations with respect to exemplary spatial locations of different exemplary sound sources.

Specifically, as shown in FIG. 4, implementation 400 of system 300 may be associated with a patient 402 (i.e. shown in FIG. 4 from a top perspective as patient 402 is facing the top of the page) having two ears 404 (i.e., a left ear 404-1 and a right ear 404-2). As shown, implementation 400 of system 300 may include two sound processors 406 (i.e., sound processor 406-1 associated with left ear 404-1 and sound processor 406-2 associated with right ear 404-2) each communicatively coupled directly with respective microphones 408 (i.e., microphone 408-1 associated with sound processor 406-1 and microphone 408-2 associated with sound processor 406-2). As shown, sound processors 406 may also be interconnected (e.g., communicatively coupled) to one another by way of a communication link 410 and may each be associated with a respective cochlear implant 412 (i.e., cochlear implant 412-1 associated with sound processor 406-1 and cochlear implant 412-2 associated with sound processor 406-2) implanted within patient 402.

Each of the elements of implementation 400 of system 300 may be similar to elements described above in relation to cochlear implant system 100. Specifically, sound processors 406 may each be similar to sound processor 104 of cochlear implant system 100, microphones 408 may each be similar to microphone 102 of cochlear implant system 100, and cochlear implants 412 may each be similar to cochlear implant 108 of cochlear implant system 100. In some examples, implementation 400 may include additional elements not explicitly shown in FIG. 4 as may serve a particular implementation. For example, respective headpieces similar to headpieces 106 of cochlear implant system 100, respective wireless communication links similar to communication link 114, respective leads having one or more electrodes similar to lead 110 having one or more electrodes 112, and so forth, may be included within or associated with various other elements of implementation 400. Additionally, as described above, communication link 410 represents a communication link (e.g., a wireless audio transmission link, a wired audio transmission link, etc.) interconnecting sound processor 406-1 and sound processor 406-2.

In operation, implementation 400 may facilitate ITD perception by patient 402 by independently detecting, processing, and simulating an audio signal using elements on the left side of patient 402 (i.e., elements of implementation 400 associated with left ear 404-1 and ending with "-1") and elements on the right side of patient 402 (i.e., elements of implementation 400 associated with right ear 404-2 and ending with "-2"). Specifically, as will be described in more detail below, when implementation 400 is in operation, sound processor 406-1 may receive a first signal directly from microphone 408-1 and receive a second signal from sound processor 406-2 (i.e., that sound processor 406-2 receives directly from microphone 408-2) by way of communication link 410. Sound processor 406-1 may then generate a first fine structure signal representative of fine structure information of the first signal and generate a second fine structure signal representative of fine structure information of the second signal. Based on the generated first fine structure signal and the generated second fine structure signal, sound processor 406-1 may generate a first timing pulse signal that sound processor 406-1 may use to represent, to patient 402, an ITD between the first signal (i.e., the signal output by microphone 408-1) and the second signal (i.e., the signal output by microphone 408-2).

In parallel with (e.g., independently from, concurrently with, etc.) the operations performed by sound processor 406-1, sound processor 406-2 may receive the second signal directly from microphone 408-2 and receive the first signal from sound processor 406-1 by way of communication link 410. Sound processor 406-2 may then generate a third fine structure signal representative of the fine structure information of the first signal and generate a fourth fine structure signal representative of the fine structure information of the second signal. For example, while generated independently from the first and second fine structure signals generated by sound processor 406-1, the third fine structure signal may be similar or identical to the first fine structure signal (i.e., because both are generated based on the first signal), and the fourth fine structure signal may be similar or identical to the second fine structure signal (i.e., because both are generated based on the second signal). Based on the generated third and fourth fine structure signals, sound processor 406-2 may generate a second timing pulse signal that sound processor 406-2 may use to represent, to patient 402, the ITD between the first signal (i.e., the signal output by microphone 408-1) and the second signal (i.e., the signal output by microphone 408-2).

Implementation 400 of system 300 may use the first timing pulse signal and the second timing pulse signal to represent the ITD to the patient in any way as may serve a particular implementation. For example, the first timing pulse signal may include a first timing pulse occurring at a first time ("$t_1$") and the second timing pulse signal may include a second timing pulse corresponding to the first timing pulse and occurring at a second time ("$t_2$"). The first timing pulse may correspond to the second timing pulse in any suitable way. For example, as will be illustrated and described in more detail below, the first time ($t_1$) may be offset from the second time ($t_2$) by a time offset amount based on the ITD between the first signal and the second signal and representative of a spatial position of a source of the audio signal being presented to the patient with respect to respective spatial positions of the first ear and the second ear of the patient. Thus, for example, if a sound arrives at ear 404-1 approximately 400 microseconds prior to arriving at ear 404-2, the first time ($t_1$) may be configured to be 400 microseconds prior to the second time ($t_2$) (i.e., the first timing pulse on the first timing pulse signal may occur 400 microseconds prior to the second timing pulse on the second timing pulse signal).

Accordingly, sound processor 406-1 may use the first timing pulse signal to represent the ITD to the patient by directing cochlear implant 412-1 to apply electrical stimulation to patient 402 (e.g., to a cochlea of patient 402 associated with left ear 404-1) at the first time ($t_1$), and sound processor 406-2 may use the second timing pulse signal to represent the ITD to the patient by directing cochlear implant 412-2 to apply electrical stimulation to patient 402 (e.g., to a cochlea of patient 402 associated with right ear 404-2) at the second time ($t_2$) that is offset from the first time by the time offset amount based on the ITD (e.g., 400 microseconds in the example described above).

To illustrate, FIG. 4 shows a sound source 414 emitting a sound 416 that may be included within or otherwise associated with an audio signal (e.g., an acoustic audio signal continually representing the sound in the air) received by implementation 400 of system 300 (e.g., by microphones 408). As shown in FIG. 4, patient 402 may be oriented so as to be directly facing a spatial location of sound source 414. Accordingly, sound 416 (i.e., a part of the audio signal representative of sound 416) may arrive approximately simultaneously at both ears 404 of patient 402 (e.g., within a few tens of microseconds) such that the ITD presented to patient 402 may be very small or nonexistent and the first and second timing pulse signals may be approximately identical.

In contrast, FIG. 5 shows a sound source 502 emitting a sound 504 that may be included within or otherwise associated with the audio signal received by implementation 400 of system 300 in a similar way as described above in relation to FIG. 4. However, as shown in FIG. 5, patient 402 may be oriented so as to be facing perpendicularly to a spatial location of sound source 502, such that sound source 502 is directly to the left of the direction that patient 402 is facing. Accordingly, sound 504 (i.e., a part of the audio signal representative of sound 504) may arrive at significantly different times at each ear 404 of patient 402 such that the ITD presented to patient 402 may be relatively large and the first and second timing pulse signals may be very distinct. For example, sound 504 may arrive at ear 404-1 at a first time ($t_1$) after sound 504 is made while sound 504 may arrive at ear 404-2 at a second time ($t_2$) after sound 504 is made. As shown in FIG. 5, because a distance 506-1 from sound source 502 to left ear 404-1 is significantly shorter than a distance 506-2 from sound source 502 to right ear 404-2, an ITD between an arrival time of sound 504 at left ear 404-1 and an arrival time of sound 504 at right ear 404-2 may be approximately equal to the amount of time sound 504 takes to travel the difference between distance 506-1 and distance 506-2, or, in other words, the time it takes to travel from left ear 404-1 to right ear 404-2, illustrated by distance 508.

Similarly, FIG. 6 shows a sound source 602 emitting a sound 604 that may be included within or otherwise associated with the audio signal received by implementation 400 of system 300 in a similar way as described above in relation to FIGS. 4 and 5. In the example of FIG. 6, patient 402 may be oriented so as to be partially, but not directly facing a spatial location of sound source 602, such that sound source 602 is slightly to the left of the direction that patient 402 is facing, and the ITD represented is somewhere between the minimal ITD of the example of FIG. 4 and the maximal ITD of the example of FIG. 5. Accordingly, sound 604 (i.e., a part of the audio signal representative of sound 604) may arrive at a slightly different times at each ear 404 of patient 402 such that the ITD presented to patient 402 may be somewhere between the small ITD of FIG. 4 and the large ITD of FIG. 5. For example, sound 604 may arrive at ear 404-1 at a first time ($t_1$) after sound 604 is made while sound 604 may arrive at ear 404-2 at a second time ($t_2$) after sound 604 is made. As shown in FIG. 6, because a distance 606-1 from sound source 602 to left ear 404-1 is slightly shorter than a distance 606-2 from sound source 602 to right ear 404-2, an ITD between an arrival time of sound 604 at left ear 404-1 and an arrival time of sound 604 at right ear 404-2 may be approximately equal to the amount of time sound 604 takes to travel the difference between distance 606-1 and distance 606-2 (not explicitly illustrated in FIG. 6).

System 300 may detect and/or represent to a patient (e.g., patient 402) the ITD between the arrival times of an audio signal (e.g., an audio signal including sound 416 of FIG. 4, 504 of FIG. 5, 604 of FIG. 6, etc.) to a first ear of the patient (e.g., left ear 404-1) and to a second ear of the patient (e.g., right ear 404-2) in any manner as may serve a particular implementation. To illustrate, FIGS. 7 and 8 illustrate examples of how implementation 400 of system 300 may encode ITD cues into one or more signals generated to direct cochlear implants within the patient to apply electrical stimulation to the patient representative of an audio signal presented to the patient.

Figure 7:
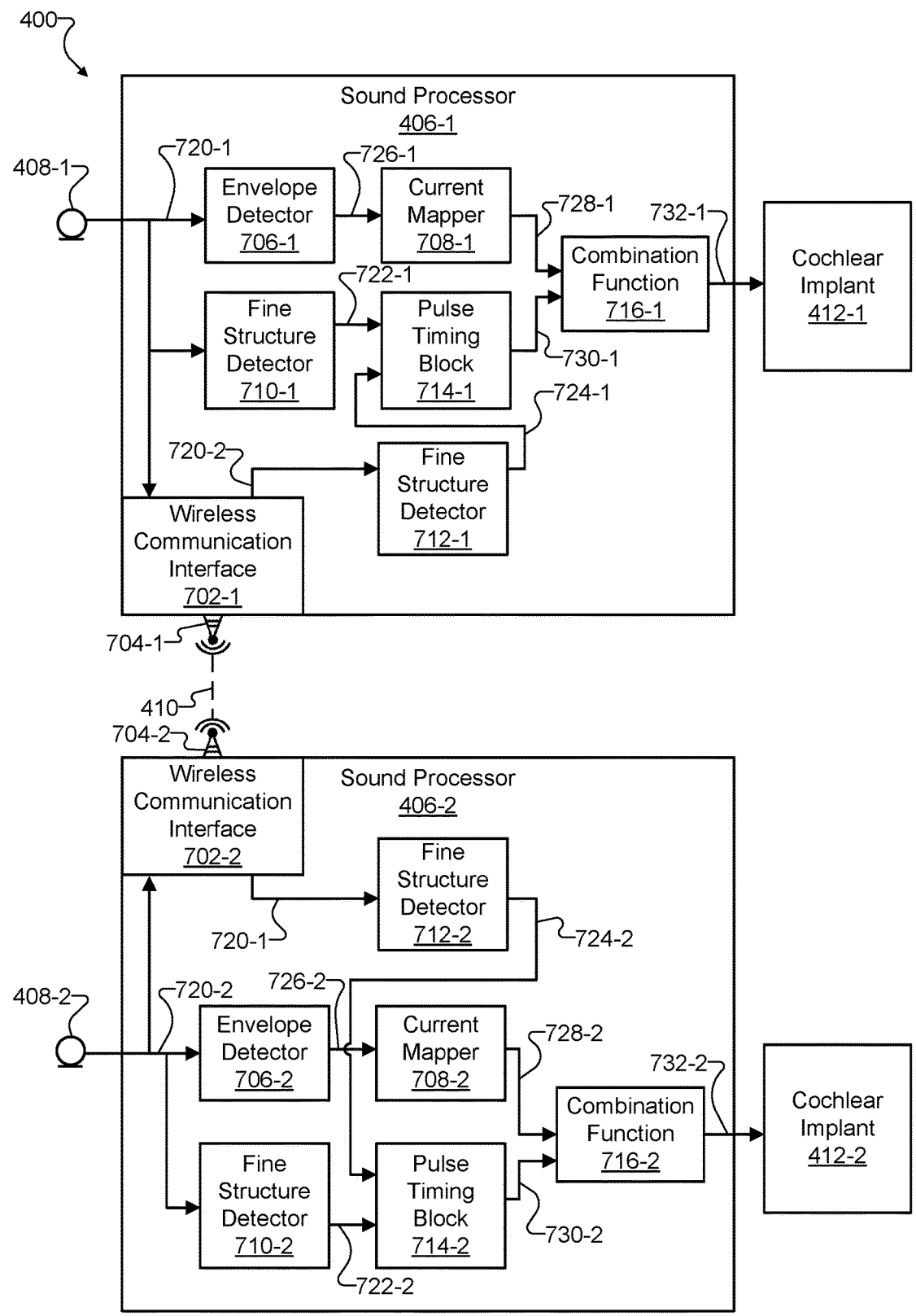
FIGS. 7-8 illustrate exemplary components of exemplary implementations of the binaural cochlear implant system of FIG. 3 according to principles described herein.
Figure 8:
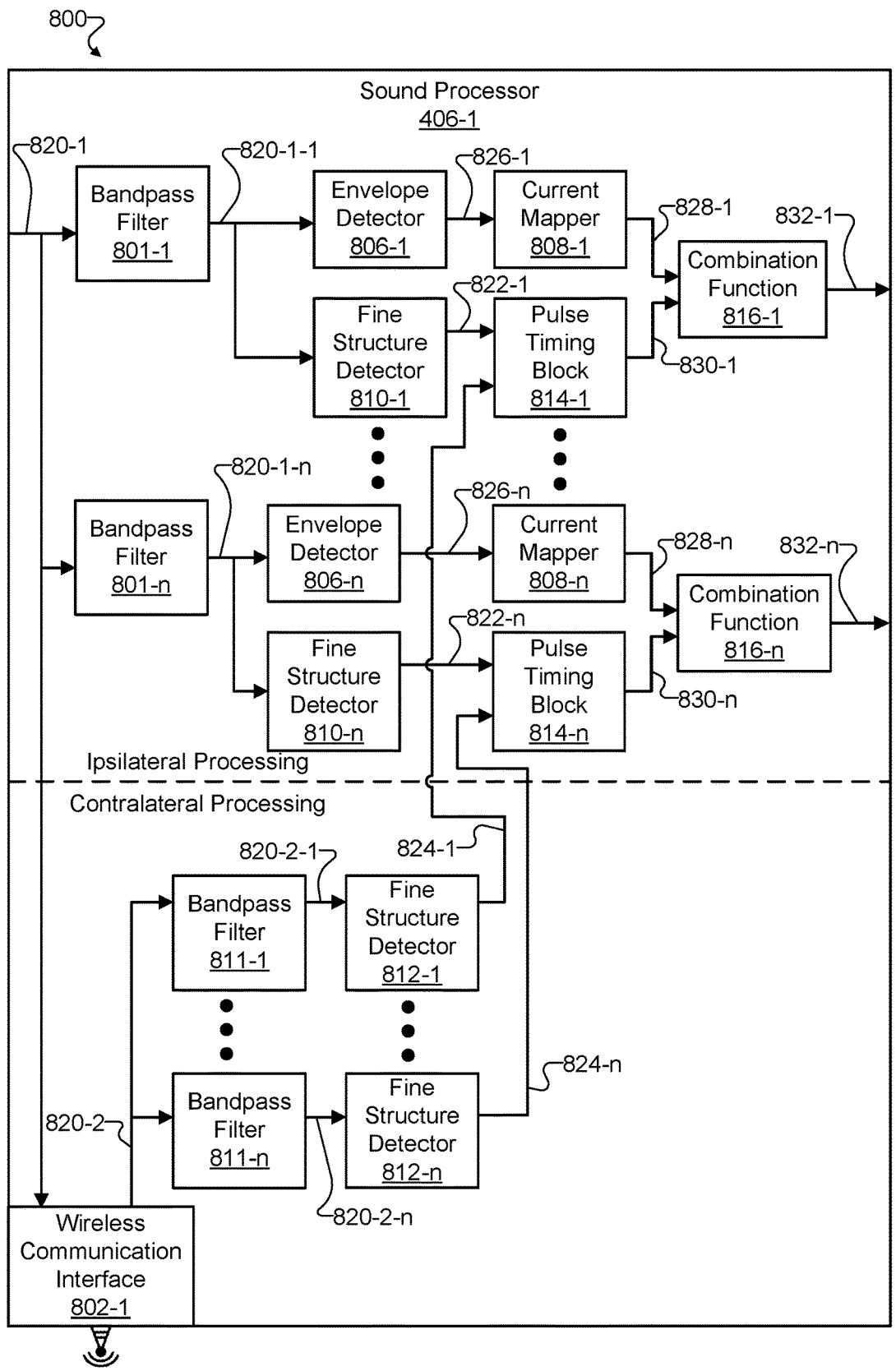

For example, FIG. 7 illustrates exemplary components of implementation 400 of system 300. Specifically, as described above, sound processors 406 (i.e., sound processors 406-1 and 406-2) of implementation 400 may receive input from respective microphones 408 (i.e., microphones 408-1 and 408-2) and may generate output to direct respective cochlear implants 412 (i.e., cochlear implants 412-1 and 412-2) to apply electrical stimulation to patient 402. Additionally, sound processors 406 may include respective wireless communication interfaces 702 (i.e., wireless communication interfaces 702-1 of sound processor 406-1 and wireless communication interface 702-2 of sound processor 406-2) each associated with respective antennas 704 (i.e., antenna 704-1 of wireless communication interface 702-1 and antenna 704-2 of wireless communication interface 702-2) to generate communication link 410, by which sound processors 406 are interconnected with one another as described above.

As further shown in FIG. 7, sound processors 406 may each include respective envelope detectors 706 (i.e., envelope detector 706-1 of sound processor 406-1 and envelope detector 706-2 of sound processor 406-2), current mappers 708 (i.e., current mapper 708-1 of sound processor 406-1 and current mapper 708-2 of sound processor 406-2), ipsilateral fine structure detectors 710 (i.e., ipsilateral fine structure detector 710-1 of sound processor 406-1 and ipsilateral fine structure detector 710-2 of sound processor 406-2), contralateral fine structure detectors 712 (i.e., contralateral fine structure detector 712-1 of sound processor 406-1 and contralateral fine structure detector 712-2 of sound processor 406-2), pulse timing blocks 714 (i.e., pulse timing block 714-1 of sound processor 406-1 and pulse timing block 714-2 of sound processor 406-2), and combination functions 716 (i.e., combination function 716-1 of sound processor 406-1 and combination function 716-2 of sound processor 406-2). Microphones 408, communication link 410, and cochlear implants 412, are each described above. The other components illustrated in FIG. 7 (i.e., components 702 through 716) will now each be described in detail.

Wireless communication interfaces 702 may use antennas 704 to transmit wireless signals (e.g., audio signals) to other devices such as to other wireless communication interfaces 702 in other sound processors 406 and/or to receive wireless signals from other such devices, as shown in FIG. 7. In some examples, communication link 410 may represent signals traveling in both directions between two wireless communication interfaces 702 on two sound processors 406. While FIG. 7 illustrates wireless communication interfaces 702 transferring wireless signals using antennas 704, it will be understood that in certain examples, a wired communication interface without antennas 704 may be employed as may serve a particular implementation.

Wireless communication interfaces 702 may be especially adapted to wirelessly transmit audio signals (e.g., signals output by microphones 408 that are representative of audio signals detected by microphones 408). For example, as shown in FIG. 7, wireless communication interface 702-1 may be configured to transmit a signal 720-1 (e.g., a signal output by microphone 408-1 that is representative of an audio signal detected by microphone 408-1) with minimal latency such that signal 720-1 is received by wireless communication interface 702-2 at approximately the same time (e.g., within a few microseconds or tens of microseconds) as wireless communication interface 702-2 receives a signal 720-2 (e.g., a signal output by microphone 408-2 that is representative of an audio signal detected by microphone 408-2) from a local microphone (i.e., microphone 408-2). Similarly, wireless communication interface 702-2 may be configured to concurrently transmit signal 720-2 to wireless communication interface 702-1 (i.e., while simultaneously receiving signal 720-1 from wireless communication interface 702-1) with minimal latency. Wireless communications interfaces 702 may employ any communication procedures and/or protocols (e.g., wireless communication protocols) as may serve a particular implementation.

Envelope detectors 706 may each receive signals 720 (i.e., envelope detector 706-1 receiving signal 720-1 and envelope detector 706-2 receiving signal 720-2) and detect, within signals 720, an energy level or envelope of signals 720. As such, envelope detectors 706 may output respective signals 726 (i.e., envelope detector 706-1 outputting signal 726-1 and envelope detector 706-2 outputting 726-2) representing the energy level or the envelope of signals 720, respectively. Signals 726 may be received by current mappers 708 (i.e., current mapper 708-1 receiving signal 726-1 and current mapper 708-2 receiving signal 726-2), which may map the energy levels of signals 720 represented by signals 726 into a stimulation current that may be applied to patient 402. The stimulation current to be applied by each respective cochlear implant 412 to patient 402 may be represented by stimulation current signals 728 output by current mappers 708 (i.e., stimulation current signal 728-1 output by current mapper 708-1 and stimulation current signal 728-2 output by current mapper 708-2).

In parallel with the determining of the audio signal energy levels and the corresponding stimulation current to be applied to patient 402, sound processors 406 may also determine timing for each sound processor 406 to apply the stimulation current using fine structure detectors 710 and 712 and pulse timing blocks 714. For example, the timing at which the stimulation current is applied may be configured to facilitate ITD perception by patient 402. Each sound processor 406 may include an ipsilateral fine structure detector 710 that receives and detects fine structure information of a signal 720 directly from the ipsilateral (i.e., same-side) microphone 408 (e.g., signal 720-1 from microphone 408-1 for ipsilateral fine structure detector 710-1, and signal 720-2 from microphone 408-2 for ipsilateral fine structure detector 710-2). Each sound processor 406 may also include a contralateral fine structure detector 712 that receives and detects fine structure information of a signal 720 received from the contralateral (i.e., opposite-side) sound processor 406 by way of communication link 410 (e.g., signal 720-2 from sound processor 406-2 for contralateral fine structure detector 712-1, and signal 720-1 from sound processor 406-1 for contralateral fine structure detector 712-2).

Accordingly, ipsilateral fine structure detectors 710 generate and output respective fine structure signals 722 representative of fine structure information of respective ipsilateral signals 720 (i.e., fine structure signal 722-1 generated by ipsilateral fine structure detector 710-1 to be representative of fine structure information of signal 720-1, and fine structure signal 722-2 generated by ipsilateral fine structure detector 710-2 to be representative of fine structure information of signal 720-2). In a similar way, contralateral fine structure detectors 712 generate and output respective fine structure signals 724 representative of fine structure information of respective contralateral signals 720 (i.e., fine structure signal 724-1 generated by contralateral fine structure detector 712-1 to be representative of fine structure information of signal 720-2, and contralateral fine structure signal 724-2 generated by contralateral fine structure detector 712-2 to be representative of fine structure information of signal 720-1).

Because each of fine structure detectors 710-1 and 712-1 generate fine structure signals based on the same signals 720 as do fine structure detectors 712-2 and 710-2, respectively (i.e., both fine structure detectors 710-1 and 712-2 generate a fine structure signal representative of fine structure information of signal 720-1, while both fine structure detectors 712-1 and 710-2 generate a fine structure signal representative of fine structure information of signal 720-2), each sound processor 406 may ultimately generate identical or similar sets of fine structure signals 722 and 724. More particularly, fine structure signal 722-1 may be identical or similar to fine structure signal 724-2, while fine structure signal 724-1 may be identical or similar to fine structure signal 722-2. To illustrate, examples of fine structure signals 722 and 724 will be shown and described in more detail below.

Each sound processor 406 may include respective pulse timing blocks 714, which may each receive respective fine structure signals 722 and 724 as inputs. In particular, as shown in FIG. 7, pulse timing block 714-1 of sound processor 406-1 may receive fine structure signals 722-1 and 724-1, while pulse timing block 714-2 of sound processor 406-2 may receive fine structure signals 722-2 and 724-2. As will be described in more detail below, pulse timing blocks 714 may compare each of the fine structure signals input to generate respective timing pulse signals 730 (i.e., timing pulse signal 730-1 generated by pulse timing block 714-1 and timing pulse signal 730-2 generated by pulse timing block 714-2). Because, as described above, fine structure signals 722-1 and 724-1 may similarly or identically represent fine structure information of signal 720-1 while fine structure signals 724-1 and 722-2 may similarly or identically represent fine structure information of signal 720-2, each of pulse timing blocks 714 may receive the same data as inputs and may output similar timing pulse signals 730. However, because ipsilateral and contralateral inputs are reversed between pulse timing block 714-1 and pulse timing block 714-2 (i.e., an ipsilateral input of pulse timing block 714-1 receives an identical or similar fine structure signal as a contralateral input of pulse timing block 714-2 and a contralateral input of pulse timing block 714-1 receives an identical or similar fine structure signal as an ipsilateral input of pulse timing block 714-2), the respective timing pulse signals 730 may differ in timing in a way that represents the ITD between signals 720-1 and 720-2. To illustrate, examples of timing pulse signals 730 output by pulse timing blocks 714 will be illustrated and described in more detail below.

Combination functions 716 each receive as input respective stimulation current signals 728 and pulse timing signals 730 (i.e., stimulation current signal 728-1 and pulse timing signal 730-1 for combination function 716-1, and stimulation current signal 728-2 and pulse timing signal 730-2 for combination function 716-2), and combine the input signals to generate respective output signals 732 (i.e., output signal 732-1 for combination function 716-1 and output signal 732-2 for combination function 716-2). For example, output signals 732 may include data representative of stimulation current derived from stimulation current signals 728 combined with data representative of timing derived from timing pulse signals 730. As shown, output signals 732 may each be transmitted, respectively, to cochlear implants 412 (i.e., output signal 732-1 to cochlear implant 412-1 and output signal 732-2 to cochlear implant 412-2) to direct cochlear implants 412 to apply particular current stimulation to patient 402 at particular times encoded into output signals 732. It will be understood that additional components and signals not explicitly shown in FIG. 7 may additionally be used in performing the operations described herein. For example, respective headpieces and wireless communication links such as headpiece 106 and wireless communication link 114 illustrated and described above in relation to FIG. 1 may be used to transmit output signals 732 to cochlear implants 412.

In some embodiments, implementation 400 may include additional components not shown in the block diagram of FIG. 7. In particular, sound processors 406 may each include additional components configured to process audio signals detected and output by microphones 408 along a plurality of analysis channels, rather than by processing the entire bandwidth of the audio signals as shown in FIG. 7. For example, each of the plurality of analysis channels may correspond to a different frequency range of audible content within the audio signal, which may be encoded by a different particular region of auditory nerve tissue (e.g., auditory nerve tissue 206 described above in relation to FIG. 2) and may be associated with one or more different electrodes (e.g., electrodes 112 described above in relation to FIG. 1) by which cochlear implants 412 may apply electrical current.

To illustrate, FIG. 8 shows an implementation 800 of sound processor 406-1 similar to the implementation illustrated in FIG. 7 except that the audio signal is processed along a plurality of analysis channels. Due to space constraints and in the interest of simplicity, FIG. 8 does not illustrate an implementation of sound processor 406-2 corresponding to implementation 800 of sound processor 406-1, nor does FIG. 8 illustrate other components described above in relation to implementation 400 of system 300 such as microphones 408, wireless communication link 410, cochlear implants 412, and the like. However, it will be understood that implementation 800 of sound processor 406-1 may be included within an implementation of system 300 in any suitable way. For example, one suitable implementation of system 300 may include implementation 800 of sound processor 406-1 and a similar implementation of sound processor 406-2 along with other elements of implementation 400 illustrated in FIGS. 4 through 7.

As shown in FIG. 8, implementation 800 of sound processor 406-1 may divide a signal 820-1 received directly from a first microphone (e.g., microphone 408-1) into a plurality of N analysis channels each corresponding to a different frequency range included in a plurality of N frequency ranges. For example, implementation 800 shows that signal 820-1 is divided into N analysis channels by passing signal 820-1 through a plurality of bandpass filters 801 (i.e., bandpass filters 801-1 through 801-n) to generate a plurality of signals 820-1 (i.e., signals 820-1-1 through 820-1-n, respectively). Additionally, implementation 800 may divide a signal 820-2 received from a second sound processor (e.g., from sound processor 406-2, not explicitly shown in FIG. 8) by way of wireless communication interface 802-1 into the plurality of N analysis channels by passing signal 820-2 through another plurality of bandpass filters 811 (i.e., bandpass filters 811-1 through 811-n) to generate another plurality of signals 820-2 (i.e., signals 820-2-1 through 820-2-n, respectively).

As with numbering schemes used for components and signals described above (e.g., in relation to FIGS. 4 through 7), signals 820 include sub-reference-numbers (e.g., "-1" or "-2") indicative of the side of patient 402 with which the signals are associated (e.g., "-1" for the first side associated with left ear 404-1, and "-2" for the second side associated with right ear 404-2). However, in contrast to numbering schemes used for previous figures, other components and signals illustrated in FIG. 8 are noted with sub-reference-numbers such as "-1" and "-n" to refer, respectively, to each of the plurality of N analysis channels (i.e., analysis channels 1 through N) for the sound processor on the first side (i.e., for sound processor 406-1 associated with left ear 404-1). Thus, unless otherwise noted, similarly numbered components within implementation 800 may be understood to correspond to (i.e., perform, for one analysis channel, similar or identical operations as) components in the implementation described above in relation to FIG. 7, and similarly numbered signals within implementation 800 may likewise be understood to correspond to (i.e., include, for one analysis channel, similar or identical data as) signals included in the implementation of FIG. 7.

Specifically, envelope detectors 806 (i.e., envelope detectors 806-1 through 806-n) may all correspond to envelope detector 706-1 of FIG. 7, current mappers 808 (i.e., current mappers 808-1 through 808-n) may all correspond to current mapper 708-1 of FIG. 7, fine structure detectors 810 (i.e., fine structure detectors 810-1 through 810-n) may all correspond to fine structure detector 710-1 of FIG. 7, fine structure detectors 812 (i.e., fine structure detectors 812-1 through 812-n) may all correspond to fine structure detector 712-1 of FIG. 7, pulse timing blocks 814 (i.e. pulse timing blocks 814-1 through 814-n) may all correspond to pulse timing block 714-1 of FIG. 7, and combination functions 816 (i.e., combination functions 816-1 through 816-n) may all correspond to combination function 716-1 of FIG. 7.

Similarly, fine structure signals 822 (i.e., fine structure signals 822-1 through 822-n) may all correspond to fine structure signal 722-1 of FIG. 7, fine structure signals 824 (i.e., fine structure signals 824-1 through 824-n) may all correspond to fine structure signal 724-1 of FIG. 7, signals 826 (i.e., signals 826-1 through 826-n) may all correspond to signal 726-1 of FIG. 7, stimulation current signals 828 (i.e., stimulation current signals 828-1 through 828-n) may all correspond to stimulation current signal 728-1 of FIG. 7, pulse timing signals 830 (i.e., pulse timing signals 830-1 through 830-n) may all correspond to pulse timing signal 730-1 of FIG. 7, and output signals 832 (i.e., output signals 832-1 through 832-n) may all correspond to output signal 732-1 of FIG. 7.

In the case of the signals generated by respective bandpass filters 801 or 811, which are associated with either the first or second sides of patient 402 and which are also associated with a particular analysis channel, multiple sub-reference-numbers are used in FIG. 8. Thus, for example, signal 820-1-n includes sub-reference-number "-1" to indicate that the signal is associated with the first side of patient 402 (e.g., the signal derives from signal 820-1, which was detected by microphone 408-1 at left ear 404-1) as well as sub-reference-number "-n" to indicate that the signal is associated with the Nth analysis channel and the Nth frequency range (e.g., the signal was generated by bandpass filter 801-n).

In the example of FIG. 8, components for processing only two analysis channels (i.e., channel 1 and channel n) are shown, but it will be understood that similar components may be employed in various implementations to process an arbitrary number of analysis channels as may serve a particular implementation. For example, certain implementations may use sixteen analysis channels (i.e., labeled 1 through 16) corresponding to sixteen particular frequency ranges or another suitable number of analysis channels corresponding to another suitable number of frequency ranges.

In operation, implementation 800 functions similarly as described above in relation to FIG. 7, except that processing is performed with respect to each of the analysis channels, rather than to the entire frequency range of the audio signal detected by the microphones. A specific example related to analysis channel 1 will now be provided. However, it will be understood that similar operations may be performed with respect to each of the other analysis channels (e.g., analysis channels 2 through N) before, after, or concurrently with the operations described below in relation to analysis channel 1.

Bandpass filter 801-1 may first divide signal 820-1 (i.e., the signal received directly from microphone 408-1) into a plurality of N analysis channels (i.e., analysis channels 1 through N) each corresponding to a different frequency range included in a plurality of frequency ranges, including analysis channel 1 corresponding to a particular frequency range included in the plurality of frequency ranges. Concurrently with bandpass filter 801-1, bandpass filter 811-1 may divide signal 820-2 (i.e., the signal received from sound processor 406-2 by way of communication link 410) into the plurality of analysis channels. Fine structure detector 810-1 may generate fine structure signal 822-1, which may be representative of fine structure information only included in a portion of signal 820-1 (i.e., a portion represented by signal 820-1-1) that is in the particular frequency range of analysis channel 1. Fine structure detector 811-1 may concurrently generate fine structure signal 824-1, which may be representative of fine structure information only included in a portion of signal 820-2 (i.e., a portion represented by signal 820-2-1) that is in the particular frequency range of analysis channel 1.

Pulse timing block 814-1 may input both fine structure signals 822-1 and 824-1 and, as will be described in more detail below, may generate timing pulse signal 830-1, which may be used to time the electrical stimulation applied to patient 402 to facilitate ITD perception by patient 402. For example, by transmitting output signal 832-1 to cochlear implant 412-1, sound processor 406-1 may direct cochlear implant 412-1 to apply electrical stimulation representative of signal 820-1-1 to patient 402 by way of one or more electrodes that correspond to analysis channel 1 at one or more times corresponding to one or more timing pulses included in timing pulse signal 830-1. More specifically, in some examples, envelope detector 806-1 and/or current mapper 808-1 may operate together to generate and output current stimulation signal 828-1 representative of an energy level of signal 820-1-1 corresponding to the particular frequency range of analysis channel 1. Using output signal 832-1, sound processor 406-1 may thus direct cochlear implant 412-1 to apply the electrical stimulation representative of signal 820-1-1 to patient 402 by directing cochlear implant 412-1 to apply electrical stimulation representative of current stimulation signal 828-1 at the one or more times corresponding to the one or more timing pulses included in timing pulse signal 830-1.

In some examples, sound processor 406-1 may use timing pulse signal 830-1 to represent an ITD between signals 820-1 and 820-2 by directing cochlear implant 412-1 to apply the electrical stimulation representative of signal 820-1-1 to the patient at the one or more times corresponding to the one or more timing pulses included in timing pulse signal 830-1 and by preventing cochlear implant 412-1 from applying electrical stimulation by way of the one or more electrodes that correspond to analysis channel 1 at one or more times corresponding to an absence of any of the one or more timing pulses included in timing pulse signal 830-1. For example, when one of the timing pulses is not included in timing pulse signal 830-1, sound processor 406-1 may not direct cochlear implant 412-1 to apply any electrical stimulation by way of the one or more electrodes that correspond to analysis channel 1, and/or may direct cochlear implant 412-1 to apply no electrical stimulation by way of the one or more electrodes. In this way, electrical stimulation may only be applied to an area of the cochlea of patient 402 corresponding to the frequency range of analysis channel 1 when a timing pulse is included in timing pulse signal 830-1. As such, the electrode firing pattern of one or more electrodes associated with analysis channel 1 of sound processor 406-1 may be based upon timing pulse signal 830-1. Concurrently, an electrode firing pattern of one or more electrodes associated with a corresponding analysis channel 1 of sound processor 406-2 may be based upon a similar timing pulse signal within sound processor 406-2 to represent ITD to patient 402, as described above.

Figure 9:
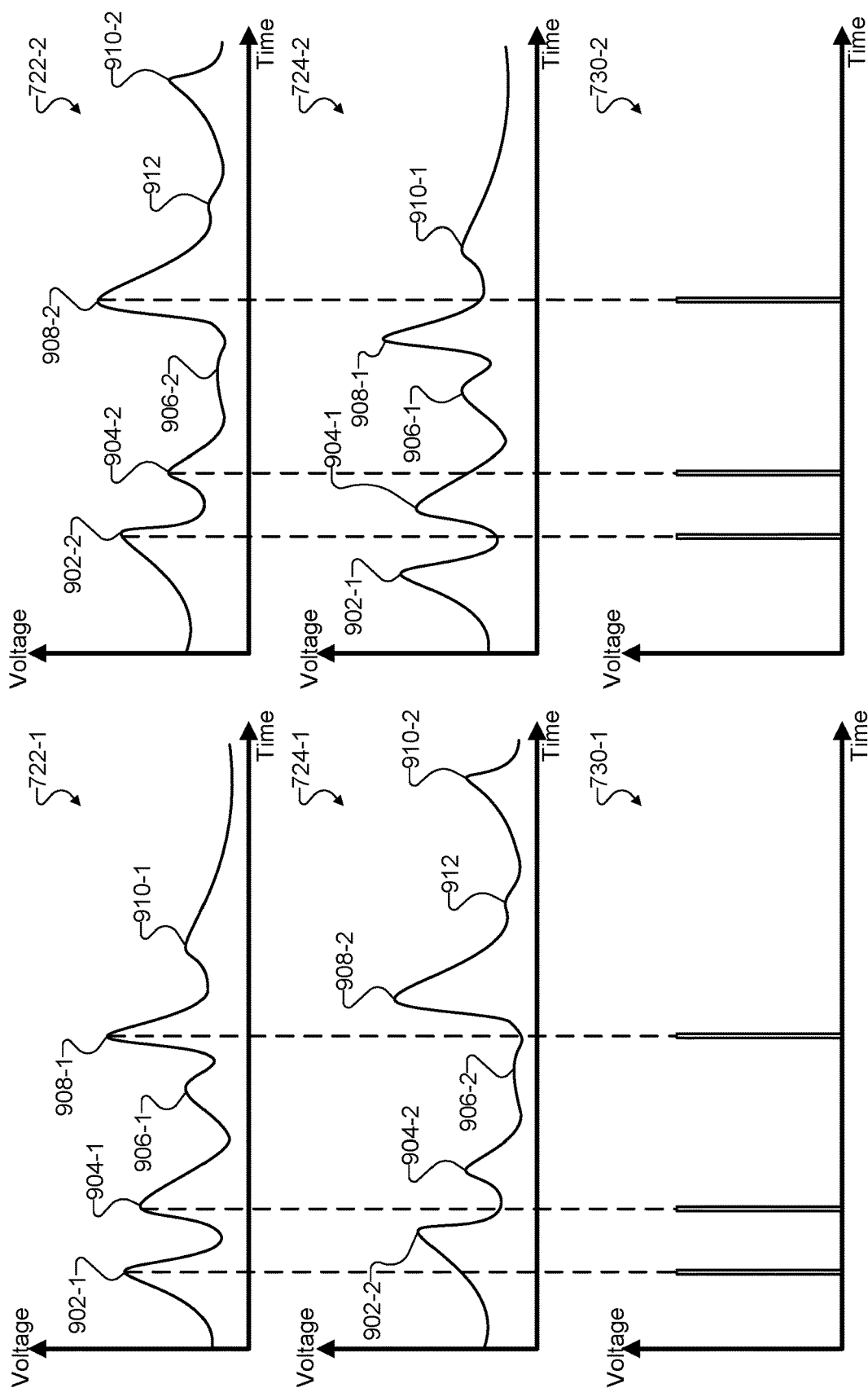
FIG. 9 illustrates exemplary fine structure signals used to generate exemplary timing pulse signals according to principles described herein.

Timing pulse signals used to control firing patterns of electrodes by cochlear implants implanted within a patient may be generated in any way as may serve a particular implementation. For example, to illustrate how pulse timing blocks (e.g., pulse timing blocks 714 and/or 814) may generate timing pulse signals (e.g., timing pulse signals 730 and/or 830, respectively), FIG. 9 shows waveforms of exemplary fine structure signals with exemplary timing pulse signals generated based on the fine structure signals, as will be described. In particular, the fine structure signals in FIG. 9 include fine structure signals 722 and 724, described above in relation to FIG. 7, and the exemplary timing pulse signals in FIG. 9 include timing pulse signals 730, which were also described above in relation to FIG. 7. FIG. 9 illustrates signals introduced and described in relation to FIG. 7 for convenience, because FIG. 7 (unlike FIG. 8) includes an illustration of basic components on both left and right sides of system 300. However, it will be understood that the same principles illustrated and described in relation to FIG. 9 for signals 722, 724, and 730, may apply equally to corresponding signals used on one or more analysis channels (e.g., analysis channels 1 through N) such as to corresponding signals illustrated and described in relation to FIG. 8 (i.e., signals 822, 824, and 830, respectively).

As described above, fine structure signals 722-1 and 724-1 are generated within sound processor 406-1 (e.g., by ipsilateral fine structure detector 710-1 and contralateral fine structure detector 712-1, respectively) to represent fine structure information of audio signals detected at left ear 404-1 and at right ear 404-2, respectively, of patient 402. Accordingly, as shown in FIG. 9, fine structure signals 722-1 and 724-1 may have certain attributes in common, such as that both signals may share certain basic features such as peaks and troughs. Specifically, as labeled on the respective signals, fine structure signals 722-1 and 724-1 include corresponding peaks such as peaks 902 (i.e., peak 902-1 on fine structure signal 722-1 and peak 902-2 on fine structure signal 724-1), peaks 904 (i.e., peak 904-1 on fine structure signal 722-1 and peak 904-2 on fine structure signal 724-1), peaks 906 (i.e., peak 906-1 on fine structure signal 722-1 and peak 906-2 on fine structure signal 724-1), peaks 908 (i.e., peak 908-1 on fine structure signal 722-1 and peak 908-2 on fine structure signal 724-1), and peaks 910 (i.e., peak 910-1 on fine structure signal 722-1 and peak 910-2 on fine structure signal 724-1).

However, as FIG. 9 also illustrates, fine structure signals 722-1 and 724-1 may also include certain differences (i.e., signals 722-1 and 724-1 are not identical). For example, peaks 902 through 910 are shown to have slightly different shapes, slightly different amplitudes, and/or slightly different durations or widths. Additionally, peaks 902-1 through 910-1 included in fine structure signal 722-1 may each be slightly offset in time from corresponding peaks 902-2 through 910-2 included in fine structure signal 724-1. These differences may be due to a variety of factors including, for example, the differences between respective media and paths traversed by sound waves between a sound source (e.g., such as sound sources 414, 502, and/or 602, described above) and each of ears 404-1 and 404-2. For instance, as illustrated in FIGS. 5 and 6, the path to ear 404-1 may be shorter than the path to ear 404-2 due to the spatial location of the sound source in relation to ears 404, and, as such, fine structure signal 724-1 may be slightly delayed as compared to fine structure signal 722-1. Additionally, different physical objects, air pressures, and so forth may be included in the path from the sound source to ear 404-1 as compared to the path from the sound source to ear 404-2.

Similarly, as shown on the right-hand side of FIG. 9, fine structure signals 722-2 and 724-2 may have also have certain attributes in common and certain differences with each other. Because fine structure signal 722-2 is representative of the same data as fine structure signal 724-1 (i.e., both are representative of fine structure information of signal 720-2, the audio signal as detected at right ear 404-2 by microphone 408-2), fine structure signals 722-2 and 724-1 may be identical or very similar. For example, as shown, signal 722-2 includes all of peaks 902-2 through 910-2 as described above in relation to fine structure signal 724-1. In the same way, because fine structure signal 724-2 is representative of the same data as fine structure signal 722-1 (i.e., both are representative of fine structure information of signal 720-1, the audio signal as detected at left ear 404-1 by microphone 408-1), fine structure signals 724-2 and 722-1 may be identical or very similar. For example, as shown, signal 724-2 includes all of peaks 902-1 through 910-1 as described above in relation to fine structure signal 722-1.

FIG. 9 illustrates how two different fine structure signals may be used to generate two different timing pulse signals that may be used to represent ITD to a patient. Specifically, FIG. 9 shows how fine structure signals 722-1 and 724-1 (or, equivalently in the context of sound processor 406-2, fine structure signals 724-2 and 722-2, respectively) can be analyzed to generate both timing pulse signals 730-1 and 730-2.

For example, timing pulse signal 730-1 may be generated by detecting peak 902-1 within fine structure signal 722-1, determining that an amplitude of peak 902-1 exceeds a predetermined amplitude threshold, detecting peak 902-2 within fine structure signal 724-1, determining that an amplitude of peak 902-2 exceeds the predetermined amplitude threshold, determining that peak 902-1 within fine structure signal 722-1 and peak 902-2 within fine structure signal 724-1 both correspond to a particular feature (e.g., a peak) of an audio signal presented to patient 402 (e.g., an audio signal detected by both microphones and represented by both signals 420-1 and 420-2). In response to determining that peak 902-1 and peak 902-2 both correspond to the particular feature of the audio signal, a first timing pulse for inclusion in timing pulse signal 730-1 may be generated (i.e., the timing pulse illustrated by the dashed line from peak 902-1 of fine structure signal 722-1). For example, the first timing pulse may be representative of an arrival time to ear 404-1 of the particular feature of the audio signal.

Similarly, timing pulse 730-2 may be generated by detecting peak 902-2 within fine structure signal 722-2, determining that an amplitude of peak 902-2 exceeds the predetermined amplitude threshold, detecting peak 902-1 within fine structure signal 724-2, determining that an amplitude of peak 902-1 exceeds the predetermined amplitude threshold, and determining that peak 902-2 within fine structure signal 722-2 and peak 902-1 within fine structure signal 724-2 both correspond to the particular feature of the audio signal presented to patient 402. In response to determining that peaks 902-2 and 902-1 both correspond to the particular feature of the audio signal, a second timing pulse for inclusion in timing pulse signal 730-2 may be generated (i.e., the timing pulse illustrated by the dashed line from peak 902-2 of fine structure signal 722-2). For example, the second timing pulse may be representative of an arrival time to ear 404-2 of the particular feature of the audio signal.

As shown in FIG. 9, additional timing pulses (e.g., pairs of corresponding pulses) may also be included in timing pulse signals 730-1 and 730-2 based on other peaks (e.g., peaks 904 and peaks 908) that are determined to exceed the predetermined amplitude threshold and to correspond to a common particular feature of the audio signal presented to patient 402. Timing pulse signals 730 and how they may be used to represent ITD to the patient will be described in more detail below.

As mentioned above, before being compared with a potential corresponding peak in a corresponding fine structure signal, a peak detected in a fine structure signal may be analyzed to determine if the peak exceeds the predetermined amplitude threshold. The predetermined amplitude threshold may include any threshold against which a detected peak may be measured as may serve a particular implementation. For example, the predetermined amplitude threshold may include a voltage level threshold (e.g., a peak-to-peak voltage level threshold, an absolute voltage level threshold, etc.), a current level threshold, or any other suitable threshold related to an amplitude of the detected peaks.

In certain examples, a feature of one or both of the fine structure signals may not exceed the predetermined amplitude threshold, and, as a result, may not be treated as a peak capable of generating a timing pulse for inclusion in timing pulse signals 730. For example, as shown in FIG. 9, peaks 906-1 and 906-2 do not correspond with respective timing pulses included in timing pulse signals 730. This may be because neither peak 906-1 nor 906-2 exceed the predetermined amplitude threshold, or because just one of the peaks (e.g., peak 906-2) fails to exceed the predetermined amplitude threshold. By not generating a timing pulse corresponding to peaks 906 and other similar peaks that fail to exceed the predetermined amplitude threshold, sound processors 406 may limit the stimulation pulse rate at which stimulation current is applied to patient 402 in order to avoid overstimulating patient 402 such that ITD cues become more difficult to perceive. Thus, in certain examples, the predetermined amplitude threshold may be set (e.g., selected) in such a way as to regulate an average pulse rate of the plurality of timing pulses included on timing pulse signals 730. For example, if the average pulse rate is too high for a particular patient (i.e., the patient receives so many ITD cues that the ITD cues become difficult to perceive), the predetermined amplitude threshold may be tightened (e.g., by raising a voltage threshold) so that fewer peaks will be detected and used to generate timing pulses and the average pulse rate will decrease. Conversely, if the average pulse rate is too low for a particular patient (i.e., the patient does not receive enough ITD to easily perceive the ITD cues), the predetermined amplitude threshold may be loosened (e.g., by lowering a voltage threshold) so that more peaks will be detected and used to generate timing pulses and the average pulse rate will increase.

As mentioned above, along with peaks being determined to exceed the predetermined amplitude threshold, peaks may also be analyzed to determine if they both correspond to a particular feature of the audio signal presented to the patient. The determination of whether a first peak within a first fine structure signal (e.g., peak 902-1 within fine structure signal 722-1) and a second peak within a second fine structure signal (e.g., peak 902-2 within fine structure signal 724-1) both correspond to the particular feature (i.e., a particular peak in the audio signal) of the audio signal presented to the patient may be performed in any way as may serve a particular implementation. For example, sound processor 406-1 (e.g., pulse timing block 414-1) may determine that the first peak is offset in time from the second peak by a time offset within a predetermined time window, or, in other words, by a time offset amount less than a predetermined time threshold.

Accordingly, as shown in FIG. 9, peaks 902, 904, and 908 are each determined to be offset in time from one another for a time offset amount small enough (i.e., smaller than the predetermined time threshold) to indicate the peaks represent the same feature of the original audio signal (as detected at different ears of patient 402). However, the offset time amount for peaks 910 may not be less than the predetermined time threshold. Certain offset time amounts may fail to be less than the predetermined time threshold for various reasons. For example, as shown in FIG. 9, peak 910-1 in fine structure signal 722-1 may actually correspond to a peak 912 included in fine structure signal 724-1 that was so small as to not even be detected as a peak, thus leaving the next peak included in fine structure signal 724-1 (i.e., peak 910-2) to compare with peak 910-1. As such, the predetermined time threshold may act as an error-correction mechanism to ensure that unrelated peaks (i.e., peaks that do not both correspond to the same particular feature of the audio signal presented to the patient) are not used to generate undesirable timing pulses. As another example, peak 910-1 in fine structure signal 722-1 may be generated by a different source than peaks 910-2 and/or 912. For instance, peak 910-1 may be generated by a "dominant" sound source (e.g., a person talking to the patient) while peaks 910-2 and/or 912 may be generated by a separate sound source (e.g., background noise, a separate person in the room talking to someone other than the patient, etc.). By using the predetermined time threshold as described above, system 300 may thus facilitate the patient in distinguishing one sound source (e.g., the dominant sound source) from another sound source (e.g., noise).

The predetermined time threshold may be set to a maximum expected ITD that may be expected between two ears of a particular patient (e.g., a time that it takes for sound to travel from one ear to the other ear of the patient) with an assumption that any time above that time threshold may be indicative of a problematic condition (e.g., an error) such as illustrated by peaks 912 and 910-2. Additionally or alternatively, the predetermined time threshold may be set (e.g., selected) to regulate an average pulse rate of a plurality of timing pulses included in respective timing pulse signals 730. For example, if the average pulse rate is too high for a particular patient (i.e., the patient receives so many ITD cues that the ITD cues become difficult to perceive), the predetermined time threshold may be tightened (e.g., by lowering the time threshold) so that fewer pairs of peaks will be determined to both correspond to the same feature of the audio signal and the average pulse rate will decrease. Conversely, if the average pulse rate is too low for a particular patient (i.e., the patient does not receive enough ITD to easily perceive the ITD cues), the predetermined time threshold may be loosened (e.g., by raising the time threshold) so that more pairs of peaks will be determined to correspond to the same feature of the audio signal and the average pulse rate will increase.

Together, timing pulse signals 730 may facilitate ITD perception by patient 402 in any suitable way. For example, sound processor 406-1 (e.g., pulse timing block 714-1) may generate timing pulse signal 730-1 based on fine structure signal 722-1 and fine structure signal 724-1 by generating a first plurality of timing pulses (e.g., also referred to herein as "ITD timing pulses") for inclusion in timing pulse signal 730-1, as described above. Each timing pulse included in the first plurality of timing pulses may be offset, from a corresponding timing pulse included in a second plurality of timing pulses generated for inclusion in timing pulse signal 730-2 by sound processor 406-2, by a time offset amount based on the ITD between signal 720-1 (upon which fine structure signal 722-1 is based) and signal 720-2 (upon which fine structure signal 724-1 is based). As further described above, sound processor 406-1 may then direct cochlear implant 412-1 to apply electrical stimulation representative of signal 720-1 to the patient at one or more times corresponding to the first plurality of timing pulses included in timing pulse signal 730-1.

Likewise, sound processor 406-2 (e.g., pulse timing block 714-2) may generate (e.g., concurrently with the generating by sound processor 406-1) timing pulse signal 730-2 based on fine structure signals 722-2 and 724-2 by generating the second plurality of timing pulses for inclusion in timing pulse signal 730-2. As mentioned above, each timing pulse included in the second plurality of timing pulses may be offset, from corresponding timing pulses included in the first plurality of timing pulses generated for inclusion in timing pulse signal 730-1 by sound processor 406-1, by a time offset amount based on the ITD between signal 720-2 (upon which fine structure signal 722-2 is based) and signal 720-1 (upon which fine structure signal 724-2 is based). Thus, sound processor 406-2 may similarly direct cochlear implant 412-2 to apply electrical stimulation representative of signal 412-2 to the patient at one or more times corresponding to the first plurality of timing pulses included in timing pulse signal 730-2.

Applying the electrical stimulation (i.e., stimulation current) to each side (e.g., each cochlea) of patient 402 in this way may facilitate ITD perception by patient 402. In particular, ITD cues may be encoded into electrical stimulation being applied to patient 402, but the ITD stimulation may be presented at a regulated pulse rate (i.e., so as to provide enough ITD cues for patient 402 to perceive the ITD but not so many ITD cues as to overwhelm the ability of patient 402 to perceive the ITD cues) and may be based on fine structure information representative of a detected audio signal presented to patient 402.

Figure 10:
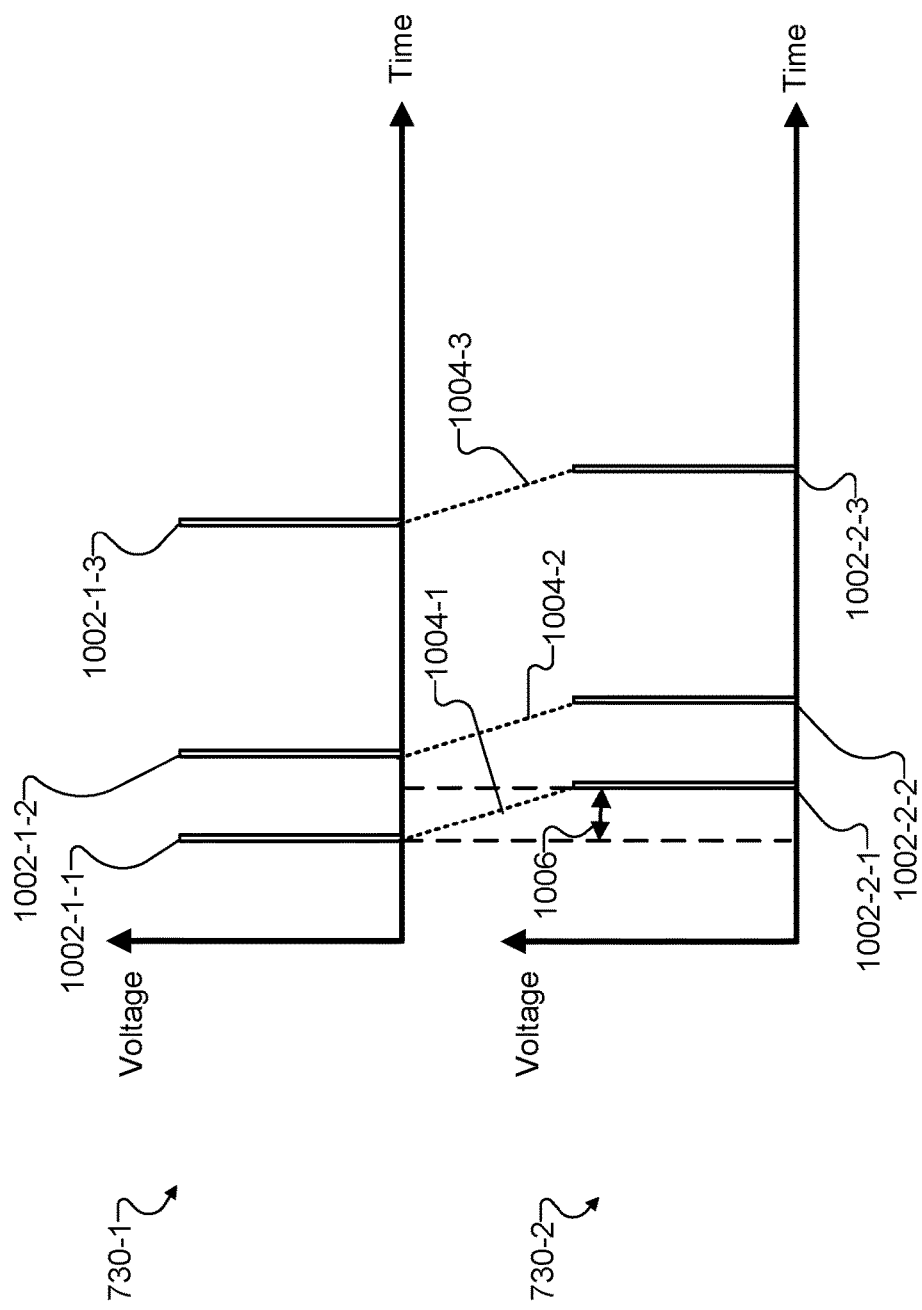
FIG. 10 illustrates an exemplary ITD of exemplary ITD timing pulses included in the timing pulse signals of FIG. 9 according to principles described herein.

To illustrate, FIG. 10 shows an exemplary ITD of exemplary timing pulses included in timing pulse signals 730. For example, as shown, timing pulse signal 730-1 includes three timing pulses 1002-1 (i.e., timing pulses 1002-1-1 through 1002-1-3) and timing pulse signal 730-2 includes three corresponding timing pulses 1002-2 (i.e., timing pulses 1002-2-1 through 1002-2-3). Timing pulses 1002-1 and 1002-2 may be referred to collectively herein as timing pulses 1002.

As described and illustrated above in relation to FIG. 9, timing pulses 1002 may come in corresponding pairs that are slightly offset in time from one another. For example, as indicated by correlation line 1004-1, timing pulses 1002-1-1 and 1002-2-1 may have both been generated based on a determination that corresponding fine structure peaks (e.g., peaks 902-1 and 902-2) exceeded a predetermined amplitude threshold and both corresponded to a particular feature of an audio signal presented to patient 402. Similarly, as indicated by correlation lines 1004-2 and 1004-3, respectively, timing pulses 1002-1-2 and 1002-2-2 and timing pulses 1002-1-3 and 1002-2-3 may have been generated based on a determination that other pairs of corresponding fine structure peaks (e.g., peaks 904-1 and 904-2, and peaks 908-1 and 908-2, respectively) exceeded the predetermined amplitude threshold and both corresponded to other particular features of the audio signal presented to patient 402.

Due to the ITD in the respective arrival times of the audio signal to ear 404-1 and ear 404-2, corresponding timing pulses 1002 are shown to be offset in time. More specifically, each of timing pulses 1002-1 included in timing pulse signal 730-1 occurs slightly before each of timing pulses 1002-2 included in timing pulse signal 730-2, such that correlation lines 1004 each slope down to the right rather than being vertical as would be the case if the pairs of timing pulses 1002 were synchronous. Thus, as electrical stimulation is applied to respective left and right cochleae of patient 402 according to electrode firing patterns based respectively on timing pulse signals 730-1 and 730-2, patient 402 may perceive an ITD 1006 between stimulation applied at times corresponding to timing pulses 1002-1-1 (at left ear 404-1) and 1002-2-1 (at right ear 404-2). Similarly, patient 402 may perceive similar ITDs (not explicitly labeled in FIG. 10) between stimulation applied at times corresponding to timing pulses 1002-1-2 and 1002-2-2 and corresponding to timing pulses 1002-1-3 and 1002-2-3.

As described above, the average pulse rates of timing pulses 1002 on timing pulse signals 730 (i.e., the average number of timing pulses 1002 included in each timing pulse signal 730 per unit of time) may be regulable. For example, the average pulse rate may be increased by loosening a predetermined amplitude threshold to cause more fine structure peaks to be analyzed as potential triggers for timing pulse generation, by loosening a predetermined time threshold to cause more pairs of fine structure peaks to be analyzed as potential triggers for timing pulse generation, and/or by otherwise modifying particular criteria upon which timing pulses may be generated as may serve a particular implementation.

However, in certain examples, it may be difficult to determine an ideal average pulse rate at which timing pulses 1002 should be regulated. For example, in order to optimize sound perception generally (e.g., speech recognition, etc.), a relatively high pulse rate (i.e., a fast electrode firing pattern for electrical stimulation) may be desirable to ensure that sufficient information is delivered to the patient for the patient to easily, conveniently, and fully perceive the information included within the audio signal presented to the patient. An adequate pulse rate in this regard may be at least somewhat dependent on a particular patient's preferences, on an environment in which the audio signal is being presented, on the type of audio signal presented (e.g., whether the audio signal includes speech), and the like, but certain patients may be most receptive to speech and other complex audio when pulse rates are, for example, greater than at least 1000 pulses per second.

At the same time, however, in order to optimize ITD perception, a relatively low pulse rate (i.e., a slow electrode firing pattern for electrical stimulation) may be desirable to ensure that the patient is not overstimulated or overwhelmed by too many ITD cues to the point that it becomes a challenge for the patient to perceive any ITD information at all. Again, an adequate pulse rate in this regard may also be at least somewhat dependent on various factors such as those described above, but certain patients may be most receptive to ITD cues when pulse rates are, for example, less than 200 pulses per second.

Consequently, for some patients and/or in certain circumstances, it may be desirable to apply current stimulation at relatively high pulse rates while introducing ITD cues at relatively low pulse rates. This may be done in any way as may serve a particular implementation. For example, referring back to FIG. 9, sound processor 406-1 may generate timing pulse signal 730-1 based on fine structure signal 722-1 and fine structure signal 724-1 by not only generating the ITD timing pulses illustrated in signal 730-1, but by also generating a first plurality of periodic timing pulses (not explicitly shown in FIG. 9) for inclusion in timing pulse signal 730-1. For example, the first plurality of periodic timing pulses may be interspersed with the first plurality of ITD timing pulses illustrated as being included in timing pulse signal 730-1, and may occur periodically based on a predetermined pulse rate. Similarly, sound processor 406-2 may generate timing pulse signal 730-2 based on fine structure signal 722-2 and fine structure signal 724-2 by not only generating the ITD timing pulses illustrated in signal 730-2, but by also generating a second plurality of periodic timing pulses (not explicitly shown in FIG. 9) for inclusion in timing pulse signal 730-2. For example, the second plurality of periodic timing pulses may be interspersed with the second plurality of ITD timing pulses illustrated as being included in timing pulse signal 730-2, and may occur periodically based on the same predetermined pulse rate.

Figure 11:
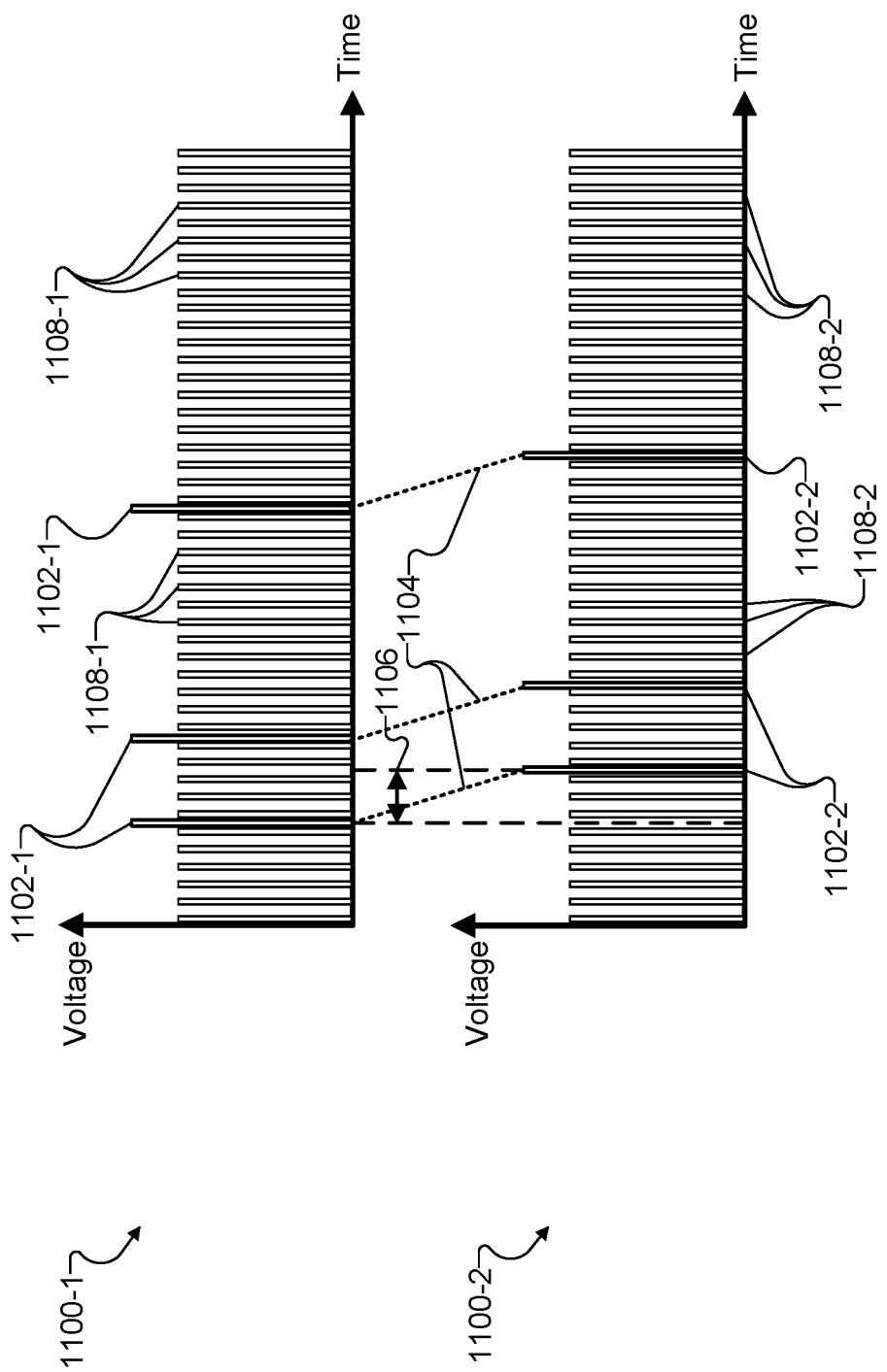
FIG. 11 illustrates exemplary periodic timing pulses interspersed with exemplary ITD timing pulses included in timing pulse signals according to principles described herein.

To illustrate, FIG. 11 shows exemplary periodic timing pulses interspersed with exemplary ITD timing pulses included in timing pulse signals. More specifically, timing pulse signals 1100 (i.e., timing pulse signals 1100-1 and 1100-2) may be similar to timing pulse signals 730 described above and, as with timing pulse signals 730, may include ITD timing pulses 1102 (i.e., timing pulses 1102-1 and 1102-2). For example, like ITD timing pulses 1002-1 and ITD timing pulses 1002-2 illustrated and described above in relation to FIG. 10, FIG. 11 illustrates ITD timing pulses 1102-1 that occur slightly before corresponding ITD timing pulses 1102-2. Additionally, as with correspondence lines 1004 and ITD 1006 in FIG. 10, FIG. 11 also shows a plurality of correspondence lines 1104 sloping down and to the right and an ITD 1106 indicative of the respective ITDs between each corresponding pair of ITD timing pulses 1102.

Unlike timing pulse signals 730 of FIG. 10, however, timing pulse signals 1100 of FIG. 11 also include, interspersed with ITD timing pulses 1102, a plurality of periodic timing pulses 1108 (i.e., periodic timing pulses 1108-1 on timing pulse signal 1100-1 interspersed with ITD timing pulses 1102-1, and periodic timing pulses 1108-2 on timing pulse signal 1100-2 interspersed with ITD timing pulses 1102-2). Periodic timing pulses 1108 may be generated at a predetermined pulse rate (e.g., a constant periodic rate) independent from the audio signal presented to the patient, and from fine structure features (e.g., peaks) of the audio signal as detected at the ears of the patient. In some examples, the predetermined pulse rate at which periodic timing pulses 1108 are generated is regulated independently from an average pulse rate at which ITD timing pulses 1102 are generated. For example, the predetermined pulse rate at which periodic timing pulses 1108 are generated may be regulated to be at least twice as high as the average pulse rate at which ITD timing pulses 1102 are generated. Indeed, as illustrated, periodic timing pulses 1108 may be generated at a relatively high pulse rate (e.g., several times higher than ITD timing pulses 1102 are generated, or over 1000 pulses per second) in order to provide a sufficiently fast electrode firing pattern to provide sufficiently detailed information representative of the audio signal to the patient.

For clarity of illustration, periodic timing pulses 1108 are illustrated as having slightly less amplitude and slightly thinner edges than ITD timing pulses 1102 in order to make the more sparse ITD timing pulses 1102 stand out amongst the more plentiful periodic timing pulses 1108 they are interspersed with. In at least some implementations, however, it will be understood that ITD timing pulses 1102 and periodic timing pulses 1108 may all have the same amplitude and may operate in the same way to direct a cochlear implant (e.g., one of cochlear implants 412) implanted within the patient (e.g., patient 402) to apply electrical stimulation to the patient at one or more times corresponding to the timing pulses. Because the human brain is capable of perceiving patterns, ITD timing pulses 1102, which do not follow the regular periodic pattern of periodic timing pulses 1108, may stand out to the patient such that ITD information encoded within ITD timing pulses 1102 may be perceived by the patient relatively easily and conveniently at a desirable ITD pulse rate (e.g., less than 200 ITD timing pulses per second), while the patient receive stimulation current representative about other aspects of the audio signal at a faster periodic pulse rate (e.g., more than 1000 periodic timing pulses per second).

Figure 12:
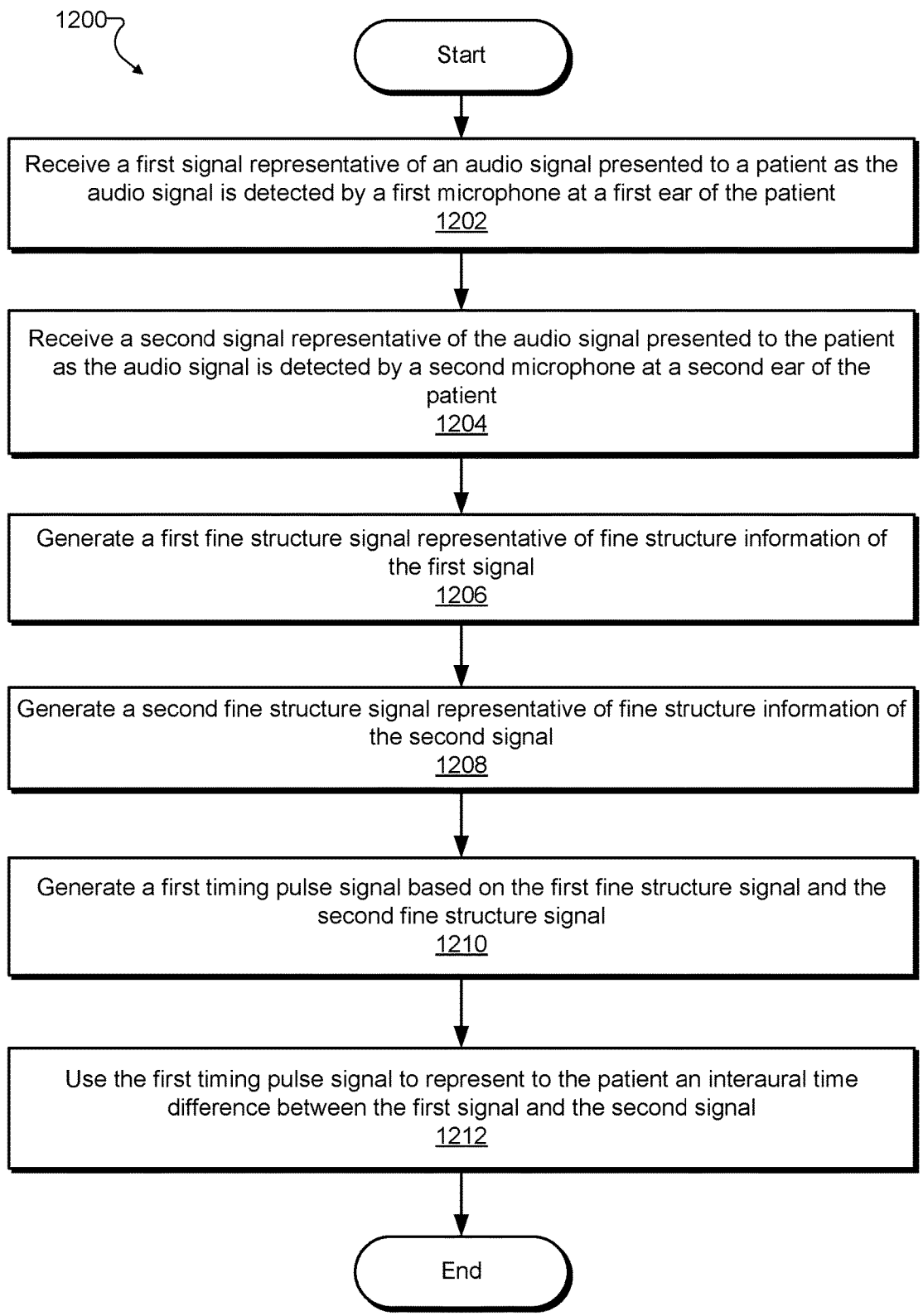
FIG. 12 illustrates an exemplary method according to principles described herein.

FIG. 12 illustrates an exemplary method 1200 for facilitating ITD perception by a binaural cochlear implant patient. While FIG. 12 illustrates exemplary operations according to one embodiment, other embodiments may omit, add to, reorder, and/or modify any of the operations shown in FIG.

12. One or more of the operations shown in FIG. 12 may be performed by system 300 and/or any implementation thereof (e.g., implementation 400). More specifically, in some examples, some or all of the operations shown in FIG. 12 may be performed by a sound processor (e.g., one of sound processors 406).

In operation 1202, a first sound processor associated with a first ear of a patient may receive a first signal directly from a first microphone associated with the first ear of the patient and communicatively coupled directly to the first sound processor. In some examples, the first sound processor may be included within a binaural cochlear implant system that further includes a second sound processor associated with a second ear of the patient. Operation 1202 may be performed in any of the ways described herein. For example, the first signal may be output by the first microphone and may be representative of an audio signal presented to the patient as the audio signal is detected by the first microphone at the first ear.

In operation 1204, the first sound processor may receive a second signal detected by a second microphone associated with the second ear of the patient and communicatively coupled directly to the second sound processor. For example, the first sound processor may receive the second signal from the second sound processor by way of a communication link that interconnects the first and second sound processors. The second signal may be output by the second microphone and may be representative of the audio signal presented to the patient as the audio signal is detected by the second microphone at the second ear. Operation 1204 may be performed in any of the ways described herein.

In operation 1206, the first sound processor may generate a first fine structure signal representative of fine structure information of the first signal. Operation 1206 may be performed in any of the ways described herein.

In operation 1208, the first sound processor may generate a second fine structure signal representative of fine structure information of the second signal. Operation 1208 may be performed in any of the ways described herein.

In operation 1210, the first sound processor may generate a first timing pulse signal based on the first fine structure signal and the second fine structure signal. Operation 1210 may be performed in any of the ways described herein.

In operation 1212, the first sound processor may use the first timing pulse signal to represent, to the patient, an interaural time difference ("ITD") between the first signal output by the first microphone and the second signal output by the second microphone. Operation 1212 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A binaural cochlear implant system comprising:
    a first microphone associated with a first ear of a patient and that
        detects an audio signal at the first ear as the audio signal is presented to the patient, and
        outputs, as the audio signal is presented to the patient, a first signal representative of the audio signal as detected by the first microphone at the first ear, the first signal including first fine structure and envelope signal elements;
    a second microphone associated with a second ear of the patient and that
        detects the audio signal at the second ear as the audio signal is presented to the patient, and
        outputs, as the audio signal is presented to the patient, a second signal representative of the audio signal as detected by the second microphone at the second ear, the second signal including second fine structure and envelope signal elements;
    a first sound processor associated with the first ear of the patient and that is communicatively coupled directly to the first microphone; and
    a second sound processor associated with the second ear of the patient and that is communicatively coupled directly to the second microphone;
    wherein the first sound processor
        receives the first signal directly from the first microphone,
        receives the second signal from the second sound processor by way of a communication link that interconnects the first and second sound processors,
        determines, based on the first and second fine structure signal elements, that a first feature of the first fine structure signal element and a second feature of the second fine structure signal element both correspond to a particular feature of the audio signal,
        generates, based on the determination that the first and second features of the respective first and second fine structure signal elements both correspond to the particular feature of the audio signal, a first timing pulse signal, and
        uses the first timing pulse signal to represent, to the patient, an interaural time difference ("ITD") between the first signal output by the first microphone and the second signal output by the second microphone.

2. The binaural cochlear implant system of claim 1, wherein the second sound processor:
    receives the second signal directly from the second microphone;
    receives the first signal from the first sound processor by way of the communication link that interconnects the first and second sound processors;
    independently determines, independent from the first sound processor and based on the first and second fine structure signal elements, that the first feature of the first fine structure signal element and the second feature of the second fine structure signal element both correspond to the particular feature of the audio signal,
    generates, based on the independent determination that the first and second features of the respective first and second fine structure signal elements both correspond to the particular feature of the audio signal, a second timing pulse signal; and
    uses the second timing pulse signal to represent, to the patient, the ITD between the first signal output by the first microphone and the second signal output by the second microphone.

3. The binaural cochlear implant system of claim 2, further comprising a first cochlear implant implanted within the patient and associated with the first ear, and a second cochlear implant implanted within the patient and associated with the second ear, wherein:

the first timing pulse signal includes a first timing pulse occurring at a first time;

the second timing pulse signal includes a second timing pulse corresponding to the first timing pulse and occurring at a second time;

the first time is offset from the second time by a time offset amount, the time offset amount based on the ITD between the first signal and the second signal and representative of a spatial position of a source of the audio signal being presented to the patient with respect to respective spatial positions of the first ear and the second ear of the patient;

the first sound processor uses the first timing pulse signal to represent the ITD to the patient by directing the first cochlear implant associated with the first ear to apply electrical stimulation to the patient at the first time; and the second sound processor uses the second timing pulse signal to represent the ITD to the patient by directing the second cochlear implant associated with the second ear to apply electrical stimulation to the patient at the second time offset from the first time by the time offset amount based on the ITD.

4. The binaural cochlear implant system of claim 1, wherein:

the generation by the first sound processor of the first timing pulse signal includes generating a first plurality of ITD timing pulses for inclusion in the first timing pulse signal, each ITD timing pulse included in the first plurality of ITD timing pulses offset, from a corresponding ITD timing pulse included in a second plurality of ITD timing pulses generated for inclusion in a second timing pulse signal by the second sound processor, by a time offset amount based on the ITD between the first signal and the second signal; and the first sound processor directs a cochlear implant implanted within the patient and associated with the first ear to apply electrical stimulation representative of the first signal to the patient at one or more times corresponding to the first plurality of ITD timing pulses included in the first timing pulse signal.

5. The binaural cochlear implant system of claim 4, wherein:

the generation by the first sound processor of the first timing pulse signal further includes generating a plurality of periodic timing pulses for inclusion in the first timing pulse signal, the plurality of periodic timing pulses interspersed with the first plurality of ITD timing pulses included in the first timing pulse signal and occurring periodically based on a predetermined pulse rate; and the first sound processor further directs the cochlear implant implanted within the patient to apply electrical stimulation representative of the first signal to the patient at one or more times corresponding to the first plurality of periodic timing pulses included in the first timing pulse signal.

6. The binaural cochlear implant system of claim 5, wherein:

the predetermined pulse rate at which the plurality of periodic timing pulses is generated is regulated independently from an average pulse rate at which the plurality of ITD timing pulses is generated; and the predetermined pulse rate at which the plurality of periodic timing pulses is generated is regulated to be at least twice as high as the average pulse rate at which the plurality of ITD timing pulses is generated.

7. The binaural cochlear implant system of claim 1, wherein the first sound processor further:

divides the first signal received directly from the first microphone into a plurality of analysis channels each corresponding to a different frequency range included in a plurality of frequency ranges, the plurality of analysis channels including a particular analysis channel corresponding to a particular frequency range included in the plurality of frequency ranges; and divides the second signal received from the second sound processor by way of the communication link into the plurality of analysis channels;

wherein the first fine structure signal element corresponds to the particular analysis channel and is representative of fine structure information only included in a portion of the first signal that is in the particular frequency range of the particular analysis channel, and the second fine structure signal element corresponds to the particular analysis channel and is representative of fine structure information only included in a portion of the second signal that is in the particular frequency range of the particular analysis channel.

8. The binaural cochlear implant system of claim 7, wherein the first sound processor directs a first cochlear implant implanted within the patient and associated with the first ear to apply electrical stimulation representative of the portion of the first signal to the patient by way of one or more electrodes that correspond to the particular analysis channel at one or more times corresponding to one or more timing pulses included in the first timing pulse signal.

9. The binaural cochlear implant system of claim 8, wherein:

the first envelope signal element is representative of an energy level of the portion of the first signal corresponding to the particular frequency range of the particular analysis channel; and the first sound processor directs the first cochlear implant to apply the electrical stimulation representative of the portion of the first signal to the patient by directing the first cochlear implant to apply electrical stimulation representative of the first envelope signal element at the one or more times corresponding to the one or more timing pulses included in the first timing pulse signal.

10. The binaural cochlear implant system of claim 8, wherein the first sound processor uses the first timing pulse signal to represent the ITD to the patient by:

directing the first cochlear implant to apply the electrical stimulation representative of the portion of the first signal to the patient at the one or more times corresponding to the one or more timing pulses included in the first timing pulse signal; and preventing the first cochlear implant from applying electrical stimulation by way of the one or more electrodes that correspond to the particular analysis channel at one or more times corresponding to an absence of any of the one or more timing pulses included in the first timing pulse signal.

11. The binaural cochlear implant system of claim 1, wherein the first sound processor determines that the first feature of the first fine structure signal element and the second feature of the second fine structure signal element both correspond to the particular feature of the audio signal by:

detecting, within the first fine structure signal element, the first feature to be a first peak;

determining that an amplitude of the first peak exceeds a predetermined amplitude threshold;
detecting, within the second fine structure signal element, the second feature to be a second peak;
determining that an amplitude of the second peak exceeds the predetermined amplitude threshold; and
determining that the first peak within the first fine structure signal element and the second peak within the second fine structure signal element both correspond to the particular feature of the audio signal presented to the patient.

12. The binaural cochlear implant system of claim 11, wherein the second sound processor:
receives the second signal directly from the second microphone;
receives the first signal from the first sound processor by way of the communication link that interconnects the first and second sound processors;
independently determines, independent from the first sound processor and based on the first and second fine structure signal elements, that the first feature of the first fine structure signal element and the second feature of the second fine structure signal element both correspond to the particular feature of the audio signal by
detecting, within the first fine structure signal element, the first feature to be the first peak,
determining that the amplitude of the first peak exceeds the predetermined amplitude threshold,
detecting, within the second fine structure signal element, the second feature to be the second peak,
determining that the amplitude of the second peak exceeds the predetermined amplitude threshold, and
determining that the first peak within the first fine structure signal element and the second peak within the second fine structure signal element both correspond to the particular feature of the audio signal presented to the patient;
generates, in response to the determining by the second sound processor that the first peak within the first fine structure signal element and the second peak within the second fine structure signal element both correspond to the particular feature of the audio signal, a second timing pulse for inclusion in a second timing pulse signal; and
uses the second timing pulse signal to represent, to the patient, the ITD between the first signal output by the first microphone and the second signal output by the second microphone.

13. The binaural cochlear implant system of claim 11, wherein the determining that the first peak within the first fine structure signal element and the second peak within the second fine structure signal element both correspond to the particular feature of the audio signal presented to the patient comprises determining that the first peak is offset in time from the second peak by a time offset amount less than a predetermined time threshold.

14. The binaural cochlear implant system of claim 13, wherein an average pulse rate of a plurality of timing pulses including the first timing pulse included in the first timing pulse signal generated by the first sound processor is regulated based on setting at least one of the predetermined amplitude threshold and the predetermined time threshold.

15. The binaural cochlear implant system of claim 1, wherein the communication link that interconnects the first and second sound processors is a wireless audio transmission link.

16. A binaural cochlear implant system comprising:
a first microphone associated with a first ear of a patient and that
detects an audio signal at the first ear as the audio signal is presented to the patient, and
outputs, as the audio signal is presented to the patient, a first signal representative of the audio signal as detected by the first microphone at the first ear;
a second microphone associated with a second ear of the patient and that
detects the audio signal at the second ear as the audio signal is presented to the patient, and
outputs, as the audio signal is presented to the patient, a second signal representative of the audio signal as detected by the second microphone at the second ear;
a first sound processor associated with the first ear of the patient and that is communicatively coupled directly to the first microphone; and
a second sound processor associated with the second ear of the patient and that is communicatively coupled directly to the second microphone;
wherein the first sound processor
receives the first signal directly from the first microphone,
receives the second signal from the second sound processor by way of a communication link that interconnects the first and second sound processors,
generates a first fine structure signal representative of fine structure information of the first signal,
generates a second fine structure signal representative of fine structure information of the second signal,
detects, within the first fine structure signal, a first peak,
detects, within the second fine structure signal, a second peak,
determines that the first peak within the first fine structure signal and the second peak within the second fine structure signal both correspond to a particular feature of the audio signal presented to the patient,
generates, in response to the determination that the first peak within the first fine structure signal and the second peak within the second fine structure signal both correspond to the particular feature of the audio signal presented to the patient, a first timing pulse for inclusion in the first timing pulse signal, the first timing pulse representative of an arrival time to the first ear of the particular feature of the audio signal, and
uses the first timing pulse signal to represent, to the patient, an interaural time difference ("ITD") between the first signal output by the first microphone and the second signal output by the second microphone.

17. The binaural cochlear implant system of claim 16, wherein the second sound processor:
receives the second signal directly from the second microphone;
receives the first signal from the first sound processor by way of the communication link that interconnects the first and second sound processors;
generates a third fine structure signal representative of the fine structure information of the first signal;
generates a fourth fine structure signal representative of the fine structure information of the second signal;
detects, within the third fine structure signal, the first peak;
detects, within the fourth fine structure signal, the second peak;

determines that the first peak within the third fine structure signal and the second peak within the fourth fine structure signal both correspond to the particular feature of the audio signal presented to the patient;

generates, based on the determination that the first peak within the third fine structure signal and the second peak within the fourth fine structure signal both correspond to the particular feature of the audio signal presented to the patient, a second timing pulse for inclusion in the second timing pulse signal, the second timing pulse representative of an arrival time to the second ear of the particular feature of the audio signal; and uses the second timing pulse signal to represent, to the patient, the ITD between the first signal output by the first microphone and the second signal output by the second microphone.

18. The binaural cochlear implant system of claim 17, further comprising a first cochlear implant implanted within the patient and associated with the first ear, and a second cochlear implant implanted within the patient and associated with the second ear, wherein:

the first timing pulse included in the first timing pulse signal occurs at a first time;

the second timing pulse included in the second timing pulse signal occurs at a second time;

the first time is offset from the second time by a time offset amount, the time offset amount based on the ITD between the first signal and the second signal and representative of a spatial position of a source of the audio signal being presented to the patient with respect to respective spatial positions of the first ear and the second ear of the patient;

the first sound processor uses the first timing pulse signal to represent the ITD to the patient by directing the first cochlear implant associated with the first ear to apply electrical stimulation to the patient at the first time; and the second sound processor uses the second timing pulse signal to represent the ITD to the patient by directing the second cochlear implant associated with the second ear to apply electrical stimulation to the patient at the second time offset from the first time by the time offset amount based on the ITD.

19. The binaural cochlear implant system of claim 16, wherein:

the first sound processor further generates a plurality of periodic timing pulses for inclusion in the first timing pulse signal, the plurality of periodic timing pulses interspersed with the first timing pulse included in the first timing pulse signal and occurring periodically based on a predetermined pulse rate; and the first sound processor uses the first timing pulse signal to represent the ITD to the patient by directing a cochlear implant implanted within the patient and associated with the first ear to apply electrical stimulation representative of the first signal to the patient at one or more times corresponding to the first timing pulse and to each of the periodic timing pulses in the plurality of periodic timing pulses included in the first timing pulse signal.

20. A method comprising:

receiving, by a first sound processor associated with a first ear of a patient and included within a binaural cochlear implant system that further includes a second sound processor associated with a second ear of the patient, a first signal directly from a first microphone associated with the first ear of the patient and communicatively coupled directly to the first sound processor, the first signal including first fine structure and envelope signal elements and output by the first microphone and representative of an audio signal presented to the patient as the audio signal is detected by the first microphone at the first ear;

receiving, by the first sound processor from the second sound processor by way of a communication link that interconnects the first and second sound processors, a second signal detected by a second microphone associated with the second ear of the patient and communicatively coupled directly to the second sound processor, the second signal including second fine structure and envelope signal elements and output by the second microphone and representative of the audio signal presented to the patient as the audio signal is detected by the second microphone at the second ear;

determining, by the first sound processor based on the first and second fine structure signal elements, that a first feature of the first fine structure signal element and a second feature of the second fine structure signal element both correspond to a particular feature of the audio signal, generating, by the first sound processor based on the determining that the first and second features of the respective first and second fine structure signal elements both correspond to the particular feature of the audio signal, a first timing pulse signal; and using, by the first sound processor, the first timing pulse signal to represent, to the patient, an interaural time difference ("ITD") between the first signal output by the first microphone and the second signal output by the second microphone.

* * * * *